US009886558B2

(12) United States Patent
Ober et al.

(10) Patent No.: US 9,886,558 B2
(45) Date of Patent: Feb. 6, 2018

(54) SYSTEM AND METHOD FOR ANALYZING DE-IDENTIFIED HEALTH CARE DATA

(71) Applicant: IMS HEALTH INCORPORATED, Danbury, CT (US)

(72) Inventors: N. Stephen Ober, Southboro, MA (US); John Grubmuller, Bedford, NH (US); Maureen Farrell, Bedford, MA (US); Charles Wentworth, Attleboro, MA (US); Thomas Gilbert, Holliston, MA (US); Kevin Barrett, Sherborn, MA (US); Steven Davis, Brookline, MA (US); Erik Nordman, Waltham, MA (US); Randell Grenier, Waltham, MA (US)

(73) Assignee: Quintiles IMS Incorporated, Danbury, CT (US)

( * ) Notice: Subject to any disclaimer, the term of this patent is extended or adjusted under 35 U.S.C. 154(b) by 0 days.

(21) Appl. No.: 14/588,491

(22) Filed: Jan. 2, 2015

(65) Prior Publication Data
US 2015/0112973 A1    Apr. 23, 2015

Related U.S. Application Data

(63) Continuation of application No. 13/925,243, filed on Jun. 24, 2013, now Pat. No. 8,930,404, which is a
(Continued)

(51) Int. Cl.
*G06F 17/30* (2006.01)
*G06F 19/00* (2011.01)
(Continued)

(52) U.S. Cl.
CPC .... *G06F 19/3487* (2013.01); *G06F 17/30554* (2013.01); *G06F 17/30592* (2013.01);
(Continued)

(58) Field of Classification Search
USPC ............... 707/607, 609, 687, 790, 813, 821
See application file for complete search history.

(56) References Cited

U.S. PATENT DOCUMENTS 3,752,904 A    8/1973 Waterbury
3,896,266 A    7/1975 Waterbury
(Continued)

FOREIGN PATENT DOCUMENTS

EP    0770967    5/1997
EP    0869637    10/1998
(Continued)

OTHER PUBLICATIONS

Hefting, Robert and Barnes, Mike, Large Scale Database Scrubbing Using Object Oriented Software Components. Journal of the American Medical Informatics Association, 1998.
(Continued)

*Primary Examiner* — Sana Al Hashemi
(74) *Attorney, Agent, or Firm* — Fish & Richardson P.C.

(57) ABSTRACT

A system and method for creating a unique alias associated with an individual identified in a health care database such that health care data, and particularly pharmaceutical-related data, can be efficiently gathered and analyzed. The system has a first store for storing at least one record where each record includes a plurality of identification fields which when concatenated uniquely identify an individual, and at least one health care field corresponding to health care data associated with the individual. The system also has a second data store, and a processor. The processor selects a record of the first data store, then selects a subset of the plurality of identification fields within the selected record, and concatenates the selected subset of identification fields. Then the processor stores the concatenated identification fields in a
(Continued)

record in the second store with at least one health care field from the selected record of the first data store.

14 Claims, 17 Drawing Sheets

Related U.S. Application Data continuation of application No. 09/665,752, filed on Sep. 20, 2000, now Pat. No. 8,473,452.

(60) Provisional application No. 60/154,726, filed on Sep. 20, 1999.

(51) Int. Cl.
G06F 21/62 (2013.01)
G06Q 10/10 (2012.01)

(52) U.S. Cl.
CPC ............ G06F 19/32 (2013.01); G06F 19/322 (2013.01); G06F 19/326 (2013.01); G06F 19/3456 (2013.01); G06F 21/6254 (2013.01); G06Q 10/10 (2013.01)

(56) References Cited

U.S. PATENT DOCUMENTS

| | | |
|---|---|---|
| 4,823,265 A | 4/1989 | Nelson |
| 4,979,832 A | 12/1990 | Ritter |
| 4,992,940 A | 2/1991 | Dworkin |
| 4,993,068 A | 2/1991 | Piosenka et al. |
| 5,003,539 A | 3/1991 | Takemoto et al. |
| 5,005,200 A | 4/1991 | Fischer |
| 5,060,263 A | 10/1991 | Bosen et al. |
| 5,070,452 A | 12/1991 | Doyle, Jr. et al. |
| 5,084,828 A | 1/1992 | Kaufman et al. |
| 5,175,681 A | 12/1992 | Iwai et al. |
| 5,202,982 A | 4/1993 | Gramlich et al. |
| 5,214,702 A | 5/1993 | Fischer |
| 5,257,369 A | 10/1993 | Skeen et al. |
| 5,265,247 A | 11/1993 | Wienck et al. |
| 5,285,494 A | 2/1994 | Sprecher et al. |
| 5,293,615 A | 3/1994 | Amada |
| 5,295,261 A | 3/1994 | Simonetti |
| 5,297,202 A | 3/1994 | Kapp et al. |
| 5,299,121 A | 3/1994 | Brill et al. |
| 5,301,105 A | 4/1994 | Cummings, Jr. |
| 5,325,290 A | 6/1994 | Cauffman et al. |
| 5,331,544 A | 7/1994 | Lu et al. |
| 5,365,589 A | 11/1994 | Gutowitz |
| 5,371,797 A | 12/1994 | Bocinsky, Jr. |
| 5,403,639 A | 4/1995 | Belsan et al. |
| 5,410,602 A | 4/1995 | Finkelstein et al. |
| 5,420,786 A | 5/1995 | Felthauser et al. |
| 5,444,823 A | 8/1995 | Nguyen |
| 5,454,101 A | 9/1995 | Mackay et al. |
| 5,471,382 A | 11/1995 | Tallman et al. |
| 5,490,060 A | 2/1996 | Malec et al. |
| 5,497,486 A | 3/1996 | Stolfo et al. |
| 5,499,293 A | 3/1996 | Behram et al. |
| 5,502,764 A | 3/1996 | Naccache |
| 5,519,607 A | 5/1996 | Tawil |
| 5,526,257 A | 6/1996 | Lerner |
| 5,557,518 A | 9/1996 | Rosen |
| 5,557,780 A | 9/1996 | Edwards et al. |
| 5,560,006 A | 9/1996 | Layden et al. |
| 5,581,749 A | 12/1996 | Hossain et al. |
| 5,606,610 A | 2/1997 | Johansson |
| 5,615,264 A | 3/1997 | Kazmierczak et al. |
| 5,634,016 A | 5/1997 | Steadham, Jr. et al. |
| 5,644,778 A | 7/1997 | Burks et al. |
| 5,652,842 A | 7/1997 | Siegrist, Jr. et al. |
| 5,664,109 A | 9/1997 | Johnson et al. |
| 5,666,492 A | 9/1997 | Rhodes et al. |
| 5,680,611 A | 10/1997 | Rail et al. |
| 5,699,428 A | 12/1997 | McDonnal et al. |
| 5,704,044 A | 12/1997 | Tarter et al. |
| 5,708,828 A | 1/1998 | Coleman |
| 5,719,938 A | 2/1998 | Haas et al. |
| 5,721,777 A | 2/1998 | Blaze |
| 5,724,575 A | 3/1998 | Hoover et al. |
| 5,734,838 A | 3/1998 | Robinson et al. |
| 5,737,539 A | 4/1998 | Edelson et al. |
| 5,745,899 A | 4/1998 | Burrows |
| 5,748,765 A | 5/1998 | Takhar |
| 5,754,938 A | 5/1998 | Herz et al. |
| 5,758,085 A | 5/1998 | Kouoheris et al. |
| 5,758,095 A | 5/1998 | Albaum et al. |
| 5,758,147 A | 5/1998 | Chen et al. |
| 5,758,355 A | 5/1998 | Buchanan |
| 5,761,500 A | 6/1998 | Gallant et al. |
| 5,781,893 A | 7/1998 | Felthauser et al. |
| 5,784,565 A | 7/1998 | Lewine |
| 5,787,186 A | 7/1998 | Schroeder |
| 5,787,435 A | 7/1998 | Burrows |
| 5,793,969 A | 8/1998 | Kamentsky et al. |
| 5,794,246 A | 8/1998 | Sankaran et al. |
| 5,799,086 A | 8/1998 | Sudia |
| 5,799,308 A | 8/1998 | Dixon |
| 5,806,074 A | 9/1998 | Souder et al. |
| 5,809,494 A | 9/1998 | Nguyen |
| 5,818,836 A | 10/1998 | DuVal |
| 5,821,871 A | 10/1998 | Benzler |
| 5,823,948 A | 10/1998 | Ross, Jr. et al. |
| 5,825,906 A | 10/1998 | Obata et al. |
| 5,826,240 A | 10/1998 | Brockman et al. |
| 5,832,449 A | 11/1998 | Cunningham |
| 5,832,494 A | 11/1998 | Egger et al. |
| 5,845,255 A | 12/1998 | Mayaud |
| 5,845,284 A | 12/1998 | Robinson |
| 5,848,373 A | 12/1998 | DeLorme et al. |
| 5,852,822 A | 12/1998 | Srinivasan et al. |
| 5,867,821 A | 2/1999 | Ballantyne et al. |
| 5,870,770 A | 2/1999 | Wolfe |
| 5,876,926 A | 3/1999 | Beecham |
| 5,890,129 A | 3/1999 | Spurgeon |
| 5,890,159 A | 3/1999 | Rekieta et al. |
| 5,897,641 A | 4/1999 | Ruddy et al. |
| 5,897,989 A | 4/1999 | Beecham |
| 5,907,677 A | 5/1999 | Glenn et al. |
| 5,911,132 A | 6/1999 | Sloane |
| 5,915,209 A | 6/1999 | Lawrence |
| 5,915,240 A | 6/1999 | Karpf |
| 5,918,208 A | 6/1999 | Javitt |
| 5,920,854 A | 7/1999 | Kirsch et al. |
| 5,923,754 A | 7/1999 | Angelo et al. |
| 5,925,810 A | 7/1999 | McBroom |
| 5,930,764 A | 7/1999 | Melchione et al. |
| 5,937,063 A | 8/1999 | Davis |
| 5,940,507 A | 8/1999 | Cane et al. |
| 5,940,835 A | 8/1999 | Sit |
| 5,956,400 A | 9/1999 | Chaum et al. |
| 5,956,716 A | 9/1999 | Kenner et al. |
| 5,961,593 A | 10/1999 | Gabber et al. |
| 5,966,695 A | 10/1999 | Melchione et al. |
| 5,970,462 A | 10/1999 | Reichert |
| 5,970,492 A | 10/1999 | Nielsen |
| 5,978,791 A | 11/1999 | Farber et al. |
| 5,987,448 A | 11/1999 | Evans et al. |
| 5,987,464 A | 11/1999 | Schneider |
| 5,987,572 A | 11/1999 | Weidner |
| 5,991,731 A | 11/1999 | Colon et al. |
| 5,991,751 A | 11/1999 | Rivette et al. |
| 5,991,758 A | 11/1999 | Ellard |
| 5,991,765 A | 11/1999 | Vethe |
| 5,995,939 A | 11/1999 | Berman et al. |
| 5,999,908 A | 12/1999 | Abelow |
| 6,003,006 A | 12/1999 | Colella et al. |
| 6,012,051 A | 1/2000 | Sammon, Jr. et al. |
| 6,014,631 A | 1/2000 | Teagarden et al. |
| 6,018,713 A | 1/2000 | Coli et al. |
| 6,021,200 A | 2/2000 | Fischer |
| 6,024,287 A | 2/2000 | Takai et al. |

(56) References Cited

U.S. PATENT DOCUMENTS

| | | |
|---|---|---|
| 6,035,306 A | 3/2000 | Lowenthal et al. |
| 6,061,658 A | 5/2000 | Chou et al. |
| 6,073,140 A | 6/2000 | Morgan et al. |
| 6,078,924 A | 6/2000 | Ainsbury et al. |
| 6,079,021 A | 6/2000 | Abadi et al. |
| 6,085,322 A | 7/2000 | Romney et al. |
| 6,088,717 A | 7/2000 | Reed et al. |
| 6,101,749 A | 8/2000 | Inbar et al. |
| 6,148,324 A | 11/2000 | Ransom et al. |
| 6,195,643 B1 | 2/2001 | Maxwell |
| 6,195,661 B1 | 2/2001 | Filepp et al. |
| 6,226,675 B1 | 5/2001 | Meltzer et al. |
| 6,249,768 B1 | 6/2001 | Tulskie, Jr. et al. |
| 6,249,769 B1 | 6/2001 | Ruffin et al. |
| 6,253,203 B1 | 6/2001 | O'Flaherty et al. |
| 6,266,675 B1* | 7/2001 | Evans ............... G06F 19/322 |
| 6,285,983 B1 | 9/2001 | Jenkins |
| 6,289,111 B1 | 9/2001 | Takhar |
| 6,295,608 B1 | 9/2001 | Parkes et al. |
| 6,302,844 B1* | 10/2001 | Walker ............... A61B 5/1112 |
| | | 128/904 |
| 6,317,700 B1 | 11/2001 | Bagne |
| 6,317,834 B1 | 11/2001 | Gennaro et al. |
| 6,321,201 B1 | 11/2001 | Dahl |
| 6,321,205 B1 | 11/2001 | Eder |
| 6,330,976 B1 | 12/2001 | Dymetman et al. |
| 6,336,114 B1 | 1/2002 | Garrison |
| 6,341,267 B1 | 1/2002 | Taub |
| 6,360,324 B2 | 3/2002 | Van Blarkom |
| 6,363,525 B1 | 3/2002 | Dougherty et al. |
| 6,397,224 B1 | 5/2002 | Zubeldia et al. |
| 6,408,263 B1 | 6/2002 | Summers |
| 6,415,280 B1 | 7/2002 | Farber et al. |
| 6,421,650 B1* | 7/2002 | Goetz ............... G06F 15/025 |
| | | 128/205.23 |
| 6,430,292 B1 | 8/2002 | Ito et al. |
| 6,434,533 B1 | 8/2002 | Fitzgerald |
| 6,449,621 B1 | 9/2002 | Pettovello |
| 6,473,609 B1 | 10/2002 | Schwartz et al. |
| 6,496,931 B1 | 12/2002 | Rajchel et al. |
| 6,523,027 B1 | 2/2003 | Underwood |
| 6,523,041 B1 | 2/2003 | Morgan et al. |
| 6,584,472 B2 | 6/2003 | Classen |
| 6,598,161 B1 | 7/2003 | Kluttz et al. |
| 6,654,721 B2 | 11/2003 | Handelman |
| 6,654,724 B1 | 11/2003 | Rubin et al. |
| 6,704,739 B2 | 3/2004 | Craft et al. |
| 6,704,740 B1 | 3/2004 | Lang |
| 6,704,873 B1 | 3/2004 | Underwood |
| 6,708,156 B1 | 3/2004 | Von Gonten |
| 6,732,113 B1 | 5/2004 | Ober et al. |
| 6,734,886 B1 | 5/2004 | Hagan et al. |
| 6,735,399 B2 | 5/2004 | Tabb et al. |
| 6,782,370 B1 | 8/2004 | Stack |
| 6,792,412 B1 | 9/2004 | Sullivan et al. |
| 6,873,979 B2 | 3/2005 | Fishman et al. |
| 6,874,085 B1 | 3/2005 | Koo et al. |
| 6,915,265 B1 | 7/2005 | Johnson |
| 6,934,687 B1 | 8/2005 | Papierniak et al. |
| 6,938,022 B1 | 8/2005 | Singhal |
| 6,988,075 B1 | 1/2006 | Hacker |
| 7,016,882 B2 | 3/2006 | Afeyan et al. |
| 7,092,896 B2 | 8/2006 | Delurgio et al. |
| 7,127,432 B2 | 10/2006 | Rubin et al. |
| 7,143,289 B2 | 11/2006 | Denning et al. |
| 7,184,947 B2 | 2/2007 | Matsuoka et al. |
| 7,200,578 B2 | 4/2007 | Paltenghe et al. |
| 7,260,215 B2 | 8/2007 | Troyansky et al. |
| 7,309,001 B2 | 12/2007 | Banfield et al. |
| 7,346,521 B2 | 3/2008 | Tolle et al. |
| 7,376,677 B2 | 5/2008 | Ober et al. |
| 7,386,526 B1 | 6/2008 | Chappel |
| 7,428,706 B2 | 9/2008 | Hagan et al. |
| 7,577,578 B2 | 8/2009 | Linde et al. |
| 7,668,820 B2 | 2/2010 | Zuleba |
| 7,865,376 B2 | 1/2011 | Ober et al. |
| 7,885,882 B1 | 2/2011 | Brander et al. |
| 8,275,850 B2 | 9/2012 | Kohan et al. |
| 8,473,452 B1 | 6/2013 | Ober et al. |
| 8,930,404 B2 | 1/2015 | Ober et al. |
| 2001/0011247 A1 | 8/2001 | O'Flaherty et al. |
| 2001/0019614 A1 | 9/2001 | Madoukh |
| 2001/0027331 A1 | 10/2001 | Thompson |
| 2001/0047281 A1 | 11/2001 | Keresman, III et al. |
| 2002/0004900 A1 | 1/2002 | Patel |
| 2002/0073099 A1 | 6/2002 | Gilbert et al. |
| 2002/0073138 A1 | 6/2002 | Gilbert et al. |
| 2002/0080968 A1 | 6/2002 | Olsson |
| 2002/0083192 A1 | 6/2002 | Alisuag |
| 2002/0116615 A1 | 8/2002 | Nguyen et al. |
| 2002/0128860 A1 | 9/2002 | Leveque et al. |
| 2002/0136407 A1 | 9/2002 | Denning et al. |
| 2002/0143794 A1 | 10/2002 | Helt |
| 2002/0165736 A1 | 11/2002 | Tolle et al. |
| 2002/0193905 A1 | 12/2002 | Davison et al. |
| 2002/0194024 A1 | 12/2002 | Kleinschmidt |
| 2002/0194025 A1 | 12/2002 | Notelovitz |
| 2002/0198473 A1 | 12/2002 | Kumar et al. |
| 2003/0021417 A1 | 1/2003 | Vasic et al. |
| 2003/0039362 A1 | 2/2003 | Califano et al. |
| 2003/0041241 A1 | 2/2003 | Saito |
| 2003/0046114 A1 | 3/2003 | Davies et al. |
| 2003/0074564 A1 | 4/2003 | Peterson |
| 2003/0081247 A1 | 5/2003 | Sharma |
| 2003/0097358 A1 | 5/2003 | Mendez |
| 2003/0120652 A1 | 6/2003 | Tifft |
| 2004/0034550 A1 | 2/2004 | Menschik et al. |
| 2004/0088355 A1 | 5/2004 | Hagan et al. |
| 2004/0117215 A1 | 6/2004 | Marchosky |
| 2004/0122726 A1 | 6/2004 | Linde et al. |
| 2004/0122792 A1 | 6/2004 | Salazar |
| 2004/0143594 A1 | 7/2004 | Kalies |
| 2004/0189707 A1 | 9/2004 | Moore et al. |
| 2004/0193905 A1 | 9/2004 | Lirov et al. |
| 2004/0199781 A1 | 10/2004 | Erickson |
| 2004/0215981 A1 | 10/2004 | Ricciardi et al. |
| 2005/0027564 A1 | 2/2005 | Yantis |
| 2005/0065912 A1 | 3/2005 | Cafrelli et al. |
| 2005/0114334 A1 | 5/2005 | Ober et al. |
| 2005/0125317 A1 | 6/2005 | Winkelman, III et al. |
| 2005/0147246 A1 | 7/2005 | Agrawal et al. |
| 2005/0165623 A1 | 7/2005 | Landi et al. |
| 2005/0216313 A1 | 9/2005 | Claud et al. |
| 2005/0234740 A1 | 10/2005 | Krishnan et al. |
| 2005/0234909 A1 | 10/2005 | Bade et al. |
| 2005/0236474 A1 | 10/2005 | Onuma et al. |
| 2005/0256740 A1 | 11/2005 | Kohan et al. |
| 2005/0256741 A1 | 11/2005 | Kohan et al. |
| 2005/0256742 A1 | 11/2005 | Kohan et al. |
| 2005/0268094 A1 | 12/2005 | Kohan et al. |
| 2005/0288964 A1 | 12/2005 | Lutzen et al. |
| 2006/0004656 A1 | 1/2006 | Lee |
| 2006/0004739 A1 | 1/2006 | Anthony et al. |
| 2006/0026156 A1 | 2/2006 | Zuleba |
| 2006/0059368 A1 | 3/2006 | Fayad et al. |
| 2006/0178892 A1 | 8/2006 | Oon |
| 2007/0073811 A1 | 3/2007 | Rubin et al. |
| 2007/0282951 A1 | 12/2007 | Selimis et al. |
| 2008/0091474 A1 | 4/2008 | Ober et al. |
| 2008/0137860 A1 | 6/2008 | Silvernail |
| 2008/0147554 A1 | 6/2008 | Stevens et al. |
| 2010/0114607 A1 | 5/2010 | Kress et al. |
| 2010/0217973 A1 | 8/2010 | Kress et al. |

FOREIGN PATENT DOCUMENTS

| | | |
|---|---|---|
| EP | 1026603 | 8/2000 |
| EP | 0884670 | 4/2002 |
| EP | 1253544 A1 | 10/2002 |
| EP | 0732014 | 5/2003 |
| EP | 1321883 A3 | 2/2004 |
| JP | 60-83847 | 3/1994 |
| JP | 7-56989 | 6/1995 |
| JP | 09-297795 | 11/1997 |

(56) References Cited

FOREIGN PATENT DOCUMENTS

| | | |
|---|---|---|
| JP | 10021302 | 1/1998 |
| JP | 10254807 | 9/1998 |
| JP | 11250165 | 9/1999 |
| JP | 2000513463 | 10/2000 |
| JP | 2000324094 | 11/2000 |
| JP | 2000514938 | 11/2000 |
| JP | 2001525614 | 12/2001 |
| JP | 2002032473 | 1/2002 |
| JP | 2003005645 | 1/2003 |
| JP | 2003173376 | 6/2003 |
| JP | 2008147364 | 6/2008 |
| JP | 2010232811 | 10/2010 |
| JP | 2011238064 | 11/2011 |
| WO | 1991005397 | 4/1991 |
| WO | 1995015628 | 6/1995 |
| WO | 1996041275 | 12/1996 |
| WO | 1996041288 | 12/1996 |
| WO | 1996042059 | 12/1996 |
| WO | 1997035271 | 9/1997 |
| WO | 1998002837 | 1/1998 |
| WO | 1998038910 | 9/1998 |
| WO | 1999037054 | 7/1999 |
| WO | 2000045317 | 8/2000 |
| WO | 2000077642 | 12/2000 |
| WO | 2001018631 | 3/2001 |
| WO | 2001018730 | 3/2001 |
| WO | 2001029692 | 4/2001 |
| WO | 2001039075 | 5/2001 |
| WO | 2001041353 | 6/2001 |
| WO | 2002063823 | 8/2002 |
| WO | 2004059555 | 7/2004 |
| WO | 2007145010 | 12/2007 |

OTHER PUBLICATIONS

Hoffman, The Formulary Model for Flexible Privacy and Access Controls, 1971.
Holman et al., "Population-Based Linkage of Health Records in Western Australia: Development of a Health Services Research Linked Database", Australian and New Zealand Journal of Public Health, vol. 23, No. 5, Oct. 1999.
IBM DB2 Universal Database, SQL Ref vol. 1 v 8.2 , 2004—833 pages.
International Search Report for PCT/US02/06268 dated Feb. 26, 2003.
International Search Report dated Feb. 6, 2007 in International Application No. PCT/US05/16094, 2 pages.
International Search Report of PCT/US00/25818.
J.D. Halamka, P. Szolovits, D. Rind, and C. Safran, A WWW Implementation of National Recommendationsa for Protecting Electronic Health Information, Journal of the American Medical Informatics Association, vol. 4, No. 6, Nov./Dec. 1997, pp. 458-464.
Jaro, Matthew, Probabilistic Linkage of Large Public Health Data Files. Statistics in Medicine, vol. 14, 1995.
Jawade et al., Securing Anonymous and Confidential Database through Privacy Preserving Updates. International Journal of Applied Information Systems, 2013.
Joshi et al., ScalParC: A New Scalable and Efficient Parallel Classification Algorithm for Mining Large Datasets, Univ. of Minn. Supercomputing Inst. (UMSI 98/14), pp. 1-20, Feb. 1998.
K. Kahl, G. Dickson, J. Kebisek and M. Powell, Bar code tracking system enhances record - and film-handling productivity, Top Health Rec Manage, vol. 12, No. 3, Mar. 1992, 1 pg., St. Joseph's Hosoital, Milwaukee, WI, PubMed—indexed for MEDLINE.
K.R. Iversen and T.O. Grotan, Socio-technical aspects of the use of health related personal information for management and research, International journal of Bio-Medical Computing, vol. 43, 1996, pp. 83-91, Elsevier Science Ireland Ltd.
Keller et al., An Algorithm for Matching Anonymous Hospital Discharge Records Used in Occupational Disease Surveillance: Anonymous Record Matching Algorithm. American Journal of Industrial Medicine 20, 1991.
Kerkri, Elmostafa, et al., Application of the Medical Data Warehousing Architecture Epidware to Epidemiological Follow-Up: Data Extraction and Transformation. Medical Informatics Europe (1999).
Kohane, Isaac, et al., Health Information Identification and De-Identification Toolkit. Journal of the American Medical Informatics Association, 1998.
Kontzalis, Identification of key attributes, gap analysis and simulation techniques in forecasting market potential of ethical pharmaceutical products, International Journal of Forecasting 8 243-249, 1992.
Non-Final Rejection dated Apr. 23, 2009 for U.S. Appl. No. 11/122,565.
Non-Final Rejection dated Apr. 27, 2009 for U.S. Appl. No. 11/122,564.
Non-Final Rejection dated Feb. 9, 2010 for U.S. Appl. No. 11/122,589.
Non-Final Rejection dated Oct. 27, 2008 for U.S. Appl. No. 11/122,589.
Notice of Appeal filed May 12, 2010 for U.S. Appl. No. 11/122,565.
Office Action dated Feb. 5, 2015 from Australian Patent Application No. 2011250762, 4 pages.
Office Action dated Jul. 28, 2014 from Canadian Patent Application No. 2564313, 5 pages.
Office Action dated Jun. 2, 2015 from corresponding Canadian Patent Application No. 2,564,313, 3 pages.
Office Action dated May 11, 2015 from corresponding European Patent Application No. 05754019.7, 4 pages.
Office Action dated Sep. 23, 2014 from Australian Patent Application No. 2011250762, 3 pages.
Office Action in Australian Application No. 2011247850, dated Sep. 4, 2014, 4 pages.
Office Action in Canadian Application No. 2564317, dated Aug. 20, 2013, 3 pages.
Office Action in Canadian Application No. 2564317, dated Jul. 28, 2014, 3 pages.
Ohrn, Aleksander and Lucila Ohno-Machado, Using Boolean Reasoning to Anonymize Databases. Artificial Intelligence in Medicine 15, 1999.
Oracle7 Release 7.3.4 Documentation Library (converted from htm files), 1997 (No Name)—2000 Pages.
Oracle7 Server Concepts Release 7.3, Feb. 1996—516 Pages.
Patent Examination Report No. 1 dated Aug. 23, 2013 from corresponding Australian Patent Application No. 2011250762, 3 pages.
Perry et al., Understanding Oracle Chapters 1,11,14, 1989.
Physicians Who Perform Medical Procedures, From Direct Medical Data, 1 pg., www.DMDdata.com.
Pommerening et al., Pseudonyms for Cancer Registries, Methods of Information in Medicine 112-121, 1996.
Privacy Data: the Data Encryption Standard Provides Valuable Protection. U.S. General Accounting Office, Program Evaluation and Methodology Division, Transfer Paper 8, Mar. 1987.
Proceedings of the 1993 Public Health Conference on Records and Statistics, Jul. 19, 1993.
Quantin et al., A Computerized Record Hash Coding and Linkage Procedure to Warrant Epidemiological Follow-Up Data Security. Medical Informatics Europe, 1997.
Quantin et al., Automatic Record Hash Coding and Linkage for Epidemiological Follow-up Data Confidentiality, 37 Methods of Information in Medicine 271-277, 1998.
Quantin, C., et al., Irreversible Encryption Method by Generation of Polynomials Medical Informatics, vol. 21, No. 2, 1996.
R. Anderson, The DeCODE Proposal for an Icelandic Health Database, Oct. 20, 1998, pp. 1-12, www.decode.is.
R. J. Anderson, A security policy model for clinical information systems, Security and Privacy, 1996, Proceedings, 1996 IEEE Symposium on Oakland, CA, USA May 6-7, 1996 (May 6, 1996), pp. 30-43, XP010164923, ISBN: 0-8186-7417-2.
Rao et al., Forecasting with a Repeat Purchase Diffusion Model, Management Science vol. 34, No. 6 , 1988.

(56) References Cited

OTHER PUBLICATIONS

Record Linkage Techniques—1997, Proceedings of an International Workshop and Exposition, Federal Committee on Statistical Methodology, Office of Management and Budget, Washington, DC (1997).
S. Chaudhuri, et al: An overview of Data Warehousing and OLAP Technology, Sigmod Record, Sigmod, New York, NY, US, vol. 26, No. 1, Mar. 1997, (Mar. 1997), pp. 65-74, XP002193792, ISSN: 0163-5808.
Samarati, Pierangela and Latanya, Sweeney, Generalizing Data to Provide Anonymity when Disclosing Information (1998).
Samarati, Pierangela and Latanya, Sweeney, Protecting Privacy when Disclosing Information: k-Anonymity and Its Enforcement through Generalization and Suppression (1998).
Scheuren et al., "HIPAA Certification for SD1's De-Identification Technology" Washington D.C. Jun. 4, 2007; oas. 1-24.
Secure Hash Standard, National Institute of Standards and Technology, Aug. 1, 2002, pp. i-iv and 1-79, Federal Information Processing Standards Publication 180-2 (+Change Notice to include SHA-224).
Segev et al., A Framework for Join Pattern Indexing in Intelligent Database Systems, IEEE Trans. on Knowledge and Data Eng'g, vol. 7, No. 6 at pp. 941-947, Dec. 1995.
Silk et al., Pre-Test-Market Evaluation of New Packaged Goods: A Model and Measurement Methodology. Journal of Marketing Research, vol. 15, Issue 2, May 1978.
Smith and Eloff, Security in Health-Care Information Systems—Current Trends. International Journal of Medical Informatics 54, 1999.
Smith, An Inquiry into the Nature and Causes of the Wealth of Nations (HeinOnline 9th ed. 1799).
Spafford, Observing Reusable Password Choices, Jul. 31, 1992.
Spenser, W., The Health Information System (HIS). Computer Programs in Biomedicine 5, 1976.
Stanberry, Ben, The Legal and Ethical Aspects of Telemedicine 2: Data Protection, Security and European Law. Journal of Telemedicine and Telecare 1998, Nov. 23, 1997.
Subramanian, Ashok, et al., Use of the World Wide Web for Multisite Data Collection. Academic Emergency Medicine, vol. 4, No. 8, Aug. 1997.
Supplementary European Search Report of EP 00 96 5216.
Sweeney, Latanya, "Datafly: A System for Providing Anonymity in Medical Data" (1997).
Sweeney, Latanya, Guaranteeing Anonymity when Sharing Medical Data, the Datafly System (1997).
Sweeney, Latanya, Maintaining Patient Confidentiality when Sharing Medical Data Requires a Symbiotic Relationship between Technology and Policy. Massachusetts Institute of Technology Artificial Intelligence Laboratory, Working Paper No. AIWP-WP344b, May 1997.
Sweeney, Latanya, Replacing Personally-Identifying Information in Medical Records, the Scrub System. Journal of the American Medical Informatics Association, 1996.
Thelot, A general solution to the linkage of anonymous data. C.R. Acad. Sci. Paris, t. 310, Serie III, 1990.
Trusted Oracle7 Release 7.1, Discussion Forum Thread, Jan. 16, 2007.
Tsukagoshi, Noboru, "Ubiquitous computing and distribution system", Magazine of "Logistic System", Japan Logistics System Institute, Jan. 30, 2004, 13(2): 32-38.
U.S. Patent and Trademark Office, Notice of Allowance for U.S. Appl. No. 09/665,752, dated Feb. 27, 2013, 13 pgs.
U.S. Patent and Trademark Office, Office Action for U.S. Appl. No. 09/665,752, dated Dec. 8, 2008, 8 pgs.
U.S. Patent and Trademark Office, Office Action for U.S. Appl. No. 09/665,752, dated Jan. 25, 2008, 7 pgs.
U.S. Patent and Trademark Office, Office Action for U.S. Appl. No. 09/665,752, dated Mar. 16, 2007, 7 pgs.
U.S. Patent and Trademark Office, Office Action for U.S. Appl. No. 09/665,752, dated May 5, 2004, 5 pgs.
U.S. Patent and Trademark Office, Office Action for U.S. Appl. No. 09/665,752, dated Mar. 4, 2005, 6 pgs.
U.S. Patent and Trademark Officer, Office Action for U.S. Appl. No. 09/665,752, dated Dec. 16, 2005, 4 pgs.
Unique Health Identifier for Individuals, U.S. Department of Health and Human Services, A White Paper, DD. 1-32, http://epic.orq/privacv/medical/hhs-id-798.html.
Urban et al., Design and Marketing of New Products, 1993.
Urban et al., Prelaunch Forecasting of New Automobiles. Management Science, vol. 36, No. 4, Apr. 1990.
Urban et al., Premarket Forecasting of Really-New Products, 60 Journal of Marketing 47-60, 1996.
Claycamp et al., Simulation Techniques in the Analysis of Marketing Strategy, Applications of the Sciences in Marketing Management (1968).
Dalenius, Tore, and Steven Reiss, "Data Swapping—a Technique for Disclosure Control," J. Statistical Planning and Inference, 1982, 6.1: 73-85.
Denning, "Field encryption and authentication," Advances in Cryptology. Springer US, 1984.
Hamilton, Deborah, "Identification and Evaluation of the Security Requirements in Medican Application", IEEE Symposium on Computer-Based Medican Systems, Jun. 1992, 12 pages.
HMS PxDx, Health Market Science, A Health Market Science Targeting Solution, 2008, 2 pgs., www.healthmarketscience.com.
Kotler, "Computer Simulation in the Analysis of New-Product Decisions," Applications of the Sciences in Marketing Management, S (1968): 283-331.
Office Action dated Apr. 26, 2016 from Australian Patent Application No. 2015201415, 4 pages.
Pfleeger, "Security in Computing," Prentice-Hall, 1989.
Physicians Treating Patients by Diagnostic Treatement Code ICD9, From Direct Medical Data, 1 pg., www.DMDdata. Com, 2008.
"Technology and Informatics 68, Medical Informatics Europe '99," Edited by Kokol et al., Published 1999, 2 pages.
Ullman, Pfleeger, Principles of Database Systems, 2d Ed., 1982, pp. 216-219.
Wohlmacher and Pharow, "Applications in Health Care Using Public-Key Certificates and Attribute Certificates," Computer Security Applications, 2000. ACSAC'00. 16th Annual Conference. IEEE, 2000.
"Person Identification Service (PIDS) (a.k.a. *Patient Identification Service*)", OMG CORBAmed DTF, Feb. 12, 1998 (No Name).
U.S. Appl. No. 11/122,581 Jan. 21, 2010 Amendment and Request for Continued Examination (RCE).
U.S. Appl. No. 11/122,581 Dec. 31, 2008 Non-Final Office Action.
U.S. Appl. No. 11/122,581 May 29, 2009 Response to Non-Final Office Action.
U.S. Appl. No. 11/122,581 Sep. 2, 2009 Final Office Action.
U.S. Appl. No. 11/122,589 Feb. 14, 2011 Amendment and Request for Continued Examination (RCE).
U.S. Appl. No. 11/122,589 Aug. 13, 2010 Non-Final Office Action.
A. Ohrm and L. Ohno-Machado, Using Boolean reasoning to ananymize databases, Artificial intelligence in Medicine, vol. 15, 1999, DD. 235-254, Elsevier Science B.V.
Allen, Computers & Security, Trusted ORACLE—Multilevel Secure Data Management for Military Computing. vol. 70, Issue 3, pp. 271-275, May 1991.
Amendment and Response and Request for Continued Examination (RCE) filed Dec. 10, 2009 for U.S. Appl. No. 11/122,589.
Amendment and Response filed Apr. 6, 2009 for U.S. Appl. No. 11/122,589.
Amendment and Response filed May 27, 2010 for U.S. Appl. No. 11/122,589.
Amendment and Response filed Oct. 23, 2009 for U.S. Appl. No. 11/122,565.
Amstutz, Management, Computers, and Market Simulation, Applications of Management Sciences in Marketing, 1970, 14 pages.
Apr. 16, 2015 Patent Examination Report No. 5 from corresponding Australian Patent Application No. 2011250761, 3 pages.
Armstrong, Brief vs. comprehensive descriptions in measuring intentions to purchase. Journal of Marketing Research, vol. 8, Issue 1, Feb. 1, 1971.

(56) References Cited

OTHER PUBLICATIONS

Atkins et al., Pharmaceutical Marketing and Media. Automation in Pharmaceutical Marketing, 1968.
Balog, Sprinter Mod III: A Model for the Analysis of New Frequently Purchased Consumer Products. Operations Research, vol. 18, No. 5, Jul. 1966.
Berger, Andreas, "Privacy Protection for Public Directory Services", Computer Networks and ISDN Systems 30, 1998.
Bertino and Foscoli, "Index Organizations for Object-Oriented Database Systems", IEEE Transactions on Knowledge and Data Engineering, vol. 7, No. 2, Apr. 1995.
Blattberg et al., Tracker: An Early Test Market Forecasting and Diagnostic Model for New Product Planning. Journal of Marketing Research, vol. 15, Issue 2, May 1978.
Bobrowski, Mastering Oracle7 & Client-Server Computing , 1994.
Borking, John, et al., Privacy-Enhancing Technologies: the Path to Anonymity, vol. II. Registratiekamer, Netherlands, Aug. 1995.
Brandt et al., Anonymous and Verifiable Registration in Databases, May 1988.
Brice et al., Choice-Adapted Preference Modelling. 2000 Sawtooth Software Conference Proceedings, 2000.
Business World, "Fighting to stay on top," Manila, Dec. 11, 1996, p. 25 (four pages total).
C. Quantin, et al. How to ensure data security of an epidemiological follow up: quality assessment of an anonymous record linkage procedure, International Journal of Medical Informatics, Elsevier Scientific Publishers, Shannon, IR, vol. 49, No. 1, Mar. 1998 (Mar. 1998), pp. 117-122, XP004149470, ISSN: 1386-5056.
Chung, Yun-Chung, et al., Intrinsic Image Extraction from a Single Image. Journal of Information Science and Engineering 25, 1939-1953 (2009).
Claycamp et al., Prediction of New Product Performance: An Analytical Approach, VI Journal of Marketing Research 414-20, 1969.
Communication Pursuant to Article 94(3) EPC dated Oct. 23, 2013 from corresponding European Patent Application No. 05 776 883.0, 6 pages.
Crosse, Marcia, et al., Medical Records Privacy, Access Needed for Health Research, but Oversight of Privacy Protections is Limited. U.S. General Accounting Office, Report to Congressional Requesters, GAO/HEHS-99-55, Feb. 24, 1999.
Dalrymple et al., Record Linkage in a Regional Mental Health Planning Study: Accuracy of Unique Identifiers, Reliability of Sociodemographics, and Estimating Identification Error. Journal of Mental Health Administration Thousand Oaks, vol. 21, Issue 2, 1994.
Denning, Cryptography and Data Security, 1982.
Dussere L., Quantin Co. & Bouzelat H., A One Way Public Key Crypto system for the Linkage of Nominal Files in Epidemiological Studies, Proceedings of the Eighth World Congress on Med. Informatics, 1995, pp. 644-647.
E.T. Carroll, S. Wright, C. Zakoworotny, Securely Implementing Remote Access within Health Information Management, Journal of AHIMA, vol. 69, No. 3, Mar. 1998, pp. 46-49, copied from the National Library of Medicine.
English Translation of Japanese Office Action for co-pending application, Reference No. B025547, Mailing No. 571403, Mailing Date: Aug. 10, 2010, Patent Application No. 2001-525614.
European Search Report dated Jul. 10, 2012 from EP Application No. 05 752 085.0, 6 pages.
Evans, Josie and Thomas MacDonald, Record-Linkage for Pharmacovigilance in Scotland. Journal of Clinical Pharmacology 47, 1999.
Fair, M.E., Record Linkage in the National Dose Registry of Canada. European Journal of Cancer, vol. 33, Suppl. 3, 1997.
Final Rejection dated Jun. 10, 2009 for U.S. Appl. No. 11/122,589.
Final Rejection dated Nov. 12, 2009 for U.S. Appl. No. 11/122,565.
Gabrieli, Guide for Unique Healthcare Identifier Model. Journal of Clinical Computing, vol. 21, No. 5, 1993.
Gertz, ECS 289F Database Systems, Security in Commercial Database Systems Chap. 3, Lecture, 1998.
H. Bouzelat, C. Quantin and L. Dusserre, Extraction and Anonymity Protocol of Medical File, Proceedings of the American Medical Informatics Association Annual Fall Symposium, 1996, pp. 323-327, AMIA, Inc.
Hamburg et al., Computer Model for New Product Demand, Harvard Business Review 107-115, 1967.
Hamilton, Deborah, "Identification and Evaluation of the Security Requirements in Medican Application", IEEE Symposium on Computer-Based Medican Systems.
Harvard Business School Case Study Johnson Wax: Enhance (A), revised Aug. 2, 1999.
Hauser et al., "Application of the "Defender" Consumer Model," Marketing Science, 1984, 3(4):327-351.
Hauser et al., A Normative Methodology for Modeling Consumer Response to Innovation. Operations Research, vol. 25, No. 4, Jul. 1977.
Hauser et al., Application, Predictive Test, and Strategy Implications for a Dynamic Model of Consumer Response. Marketing Science, vol. 1, No. 2, 1982.
Hauser et al., Consumer Oriented Transportation Service Planning: Consumer Analysis and Strategies. Applications of Management Science, vol. 1, 1981.
Hauser et al., Dynamic Analysis of Consumer Response to Marketing Strategies. Management Science, vol. 28, No. 5, May 1982.
Kotz, David, Technological Implications for Privacy, Jan. 3, 1999.
Lawrenson et al., Clinical Information for Research; the Use of the General Practice Databases. Journal of Public Health Medicine, vol. 21, No. 3, (1999).
Lennon, Functional Magic-Tips and Tricks with Oracle 7 Stored Procedures, 1996.
Levi, Albert, Design and Performance Evaluation of the Nested Certification Scheme and Its Application in Public Key Infrastructures. Ph.D. Dissertation, 1999.
Lilien et al., Bayesian Estimation and Control of Detailing Effort in a Repeat Purchase Diffusion Environment. Management Science, vol. 27, No. 5, May 1981.
Lilien et al., Marketing Decision Making, A model-Building Approach, 1983.
Lilien et al., Marketing Engineering—Computer Assisted Marketing Analysis and Planning, 1998.
Lilien et al., Marketing Models, 1992.
Lowrance, William, "Privacy and Health Research" (1998).
Mahajan et al., Innovation Diffusion and New Product Growth Models in Marketing. Journal of Marketing, vol. 43, No. 4, 1979.
Max G. Arellano, MA, and Gerald I. Weber, PhD, "Issues in Identification and Linkage of Patient Records Across an Integrated Delivery System," Journal of Healthcare Information Management, vol. 12, No. 3, Fall 1998.
McDonald, Clement et al., The Regenstrief Medical Record System: A Quarter Century Experience. International Journal of Medical Informatics 54, 1999.
Medical Radar International, Mar. 29, 1997.
Medical Radar, Guide to Success, Mar. 2, 1999.
Merkle, R. et al. "On the Security of Multiple Encryption" Communications of the ACM , vol. 24 No. 7, Jul. 1981, pp. 465-467.
Meux, Eleanor, Encrypting Personal Identifiers. Health Services Research 29:2, Jun. 1994.
Montgomery et al., Management Science in Marketing, 1969.
Muse et al., Evaluating the Quality of Anonymous Record Linkage Using Deterministic Procedures with the New York State AIDS Registry and a Hospital Discharge File. Statistics in Medicine, vol. 14, 1995.
National Institute of Standards and Technology (NIST), "Secure Hash Standard" Federal Information Processing Standards Publication 180-2 ( + Change Notice to include SHA-224), Aug. 1, 2002; pp. i-iv and 1-79.
Newswire, "CUNO Posts Record Results" New York, Dec. 11, 1997, p. 1 (seven pages total).
Nisbett et al., Telling More than We Can Know: Verbal Reports on Mental Processes. Psychological Review, vol. 84, No. 3, May 1977.

(56) References Cited

OTHER PUBLICATIONS

Urban, Sprinter Mod III: A Model for the Analysis of New Frequently Purchased Consumer Products. Operations Research, vol. 18, No. 5, Sep. 1970.
V.M. Brannigan and B. R. Beier, Patient privacy in the era of medical computer networks: a new paradigm for a new technology, Proceedings of the Eighth World Congress on Medical Informatics, vol. 8, No. 8, Jul. 23, 1995 (Jul. 23, 1995), Jul. 27, 1995 (Jul. 27, 1995), pp. 640-643, XP009040274, Vancouver, British Columbia, Canada, ISSN: 1569-6332.
Valduriez, Join Indices, ACM Trans. on Database Sys., vol. 2, No. 2 at pp. 218, 246 (1987).
Vinod, ATMSIM: A Simulator for ATM Networks. Master's Thesis (Apr. 1995).
Why Clearinghouses Transmit Electronic Claims to Insurance Carriers, and Why the Service They Provide is Essential to Medical Practices, Electronic Claim Clearinghouses, MPM Soft, Practice Billing Software, pp. 1-7, www.mpmsoft.com/EDI/clearinghouse.htm, printed Jan. 5, 2009.
Wind et al., Courtyard by Marriott: Designing a Hotel Facility with Consumer-Based Marketing Models. Interfaces 19, Jan. 1989.
X. Thirion, R. Sambuc & J.L. San Marco, Epidemiology and anonymity: a new method, Rev. Epidem. Et. Sante Publ., 1988, pp. 36-42.

\* cited by examiner

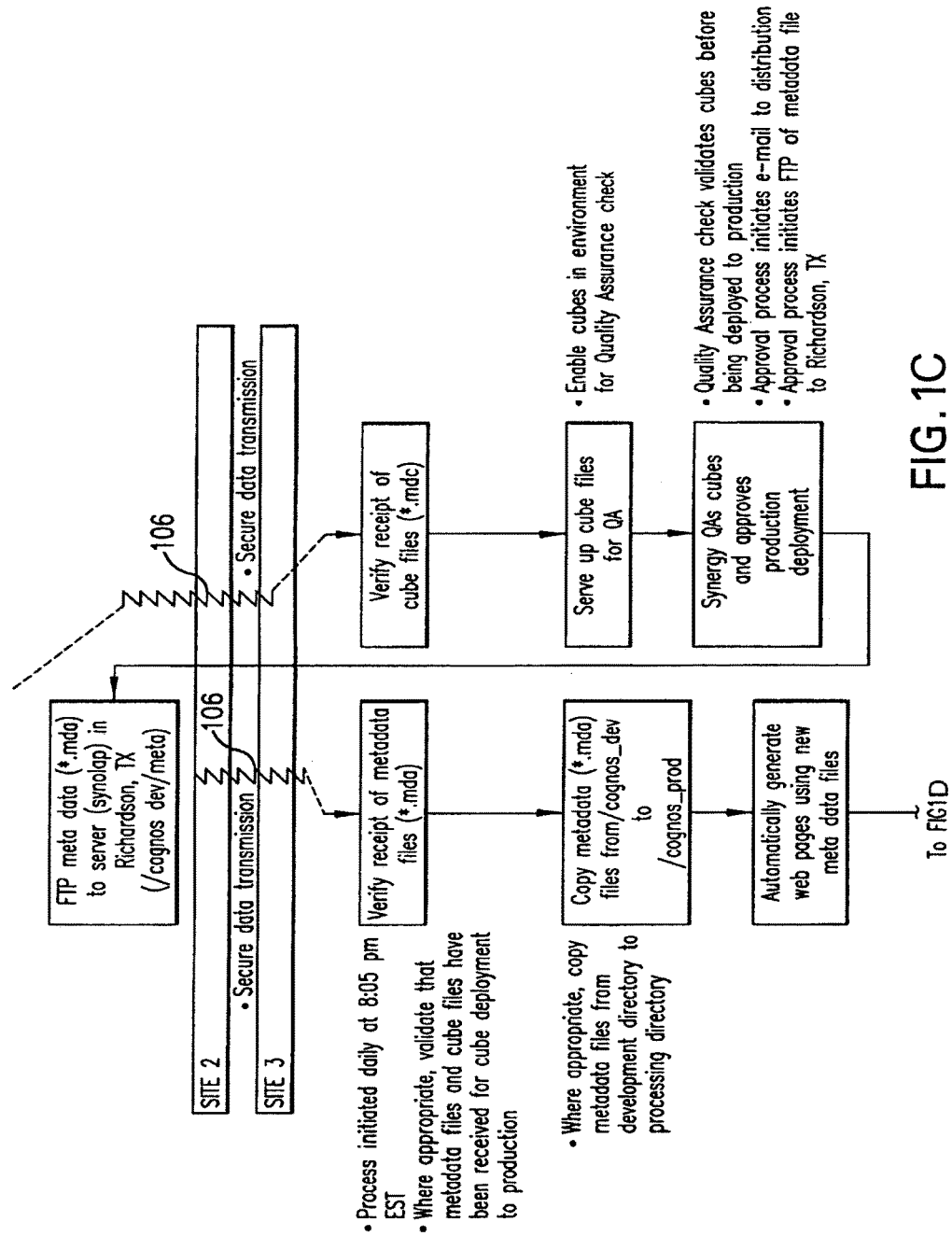

SYSTEM AND METHOD FOR ANALYZING DE-IDENTIFIED HEALTH CARE DATA

CROSS-REFERENCE TO RELATED APPLICATIONS

This application is a continuation application of and claims priority to U.S. application Ser. No. 13/925,243, filed on Jun. 24, 2013, which application is a continuation application of and claims priority to U.S. application Ser. No. 09/665,752, filed on Sep. 20, 2000, which application claims the benefit of U.S. Provisional Application Ser. No. 60/154,726, filed Sep. 20, 1999, the entireties of which applications are incorporated herein by reference.

BACKGROUND OF THE INVENTION

1. Field of the Invention

The present invention generally relates to computer systems and databases. More particularly, the present invention relates to a system and method for the gathering and analysis of health-care related data, and specifically the gathering and analysis of information regarding the use of pharmaceuticals by individuals. The present invention also relates to techniques for de-identifying the individuals from such pharmaceutical data, in order to maintain privacy.

2. Description of the Related Art

In the medical information field, pharmaceutical claims are processed on large computer systems which receive claims data for patients who have been prescribed one or more medications and have filed claims with insurance companies (or government entities) in order to have the claim paid by the company or entity. The claims data includes very specific details and attributes about the individuals making the claims. For example, attributes can include name, gender, birth date, address, medical diagnosis, specific drug prescribed, and other drugs the patient is using. Consequently, this data is very useful in assisting marketing research relative to usage of a specific drug and identifying various attributes that impact the usage.

The claims data is typically received at a data "clearinghouse" which can be a database for a specific insurance company or a larger database providing the claim processing service for many insurance companies. Moreover, the claims data that are produced by claimants include a significant amount of data, with millions of new claims being entered into the system each month. Several of the claims data clearinghouses have systems handling many terabytes of claims data. Because of the large size of the data being produced and the large amount of attributes, the data is in an inadequate format for efficient search, retrieval and analysis of specific attributes.

Recently, there have been laws passed that prevent the transmission of personal information associated with individuals, within health care claims data. This legislation particularly prohibits the transfer of specific personal data such as names, addresses and social security numbers. Thus, the claims data is no longer allowed to be transmitted from the clearinghouse to others in raw form with the personal data. Without the personal information to segregate the claims data, it becomes much harder to generate valuable research and market data based upon the unique attributes for specific individuals, such as age, gender and geographic distribution.

It is therefore desirous to provide the ability to efficiently gather information from the claims databases to allow research and analysis of the attributes that effect the pharmaceutical industry. Accordingly, the present invention is primarily directed to systems and methods for overcoming the problems discussed above, as well as related limitations of the prior art.

SUMMARY OF THE INVENTION

In one embodiment, the present invention is directed to a system and method for creating a unique alias associated with an individual identified in a health care database, that allows the aggregation of segregated data for marketing research. The system may include a first data store for storing at least one record where each record has a plurality of identification fields, such as name and birth date, which when concatenated uniquely identify an individual, and at least one health care field corresponding to health care data associated with the individual, such as a medication type. The system may also have a second data store and a processor that selects a record of the first data store, selects a subset of the plurality of identification fields within the selected record, concatenates the selected subset of identification fields, and stores the concatenated identification fields in a record in the second data store along with at least one health care field from the selected record of the first data store. The first data store and the second data store can either be located within the same database or in separate databases.

The health care data stored within the first data store may, in one embodiment, correspond to pharmaceutical claims data. The selected subset may correspond to a specific person in the healthcare database, and the person's last name, birthday, and gender are concatenated to form a unique identifier for that record. The processor may analyze longitudinal and historical records of individuals using individual-level linking methodologies based on the concatenated identification fields and the at least one health care field of each record of the second data store. The health care data also can have personal data removed from the various records such that only medically significant information remains, and the identifier allows the medical information to be segregated such that the individual records are still identifiable.

In order to more efficiently process the tremendous amount of data of the health care records, the processor may perform the further steps of selectively gathering the records from the first data store and selectively manipulating the records into a data cube. The records of the first data store are typically in tabular form, and the process of manipulating the records comprises selectively joining and projecting records from the various tabular records in the first data store to ultimately form a data cube comprised of a table of records. The data cube format allows the processor to more easily perform a search of the health care records, and also generate a report by displaying the records 25 of a specific data cube.

The present invention thus provides a method for creating a unique alias associated with an individual identified in a health care database, wherein the health care database stores at least one record, and each record has a plurality of identification fields which when taken together uniquely identify an individual, and at least one health care field may correspond to health care data associated with the individual. The method includes the steps of selecting a record within the health care database, selecting a subset of the plurality of identification fields within the selected record, concatenating the selected subset of identification fields, and storing the concatenated identification fields in a record in a second database with the at least one health care field from the selected record of the first data store. The method preferably includes the step of analyzing longitudinal, historical records of individuals using individual level linking methodologies based on the concatenated identification fields and the at least one health care field of each record of the second database.

The step of selecting a record within the health care database may comprise selecting a record from pharmaceutical claims data. Further, the step of concatenating the selected subset of identification fields may comprise, for example, concatenating, for a specific person in the healthcare database, that person's last name, birthday, and gender. Thus, based on the concatenated identification fields and the at least one health care field of each record of the second data store, the method may include the step of analyzing longitudinal, historical records of individuals using individual-level linking methodologies.

As discussed above, the method further may include the steps of selectively gathering the records from the first data store, and selectively manipulating the records into a data cube. The step of selecting a record within the health care database may comprise selecting records of the first data store that are in tabular form, and the step of selectively manipulating the records into a data cube may comprise selectively joining and projecting records from the first data store and creating a data cube comprising a table of records.

The data cube allows the present system to aggregate the records in an efficient format such that all new records can be viewed shortly after posting. Further, the unique population identifiers allow users to follow patients over time yielding important results unavailable in other databases, such as patient drug switching behavior. By linking medical and pharmacy transactions at the patient level, new insights such as indication specific use of drugs and patient comorbidities can be determined.

The report displayed by the system may contain several attributes, such as: market shares geographic information at the national, regional, state and MSA levels; trends over time including annual, quarterly, monthly, and weekly periods; traditional measures such as total, new and refilled prescription counts; source of business such as new prescription starts, switches, and continuing patients; prescriber specialty; patient demographics for age and gender; indication specific use; and patient comorbidities. The system can therefore be used in a number of ways to help make business decisions, such as monitoring new drug launches and marketing campaigns, enhanced sales force targeting, and micro-marketing in select geographic areas or to select customers. Furthermore, the system can be used for forecasting and development of a pharmaceutical marketing strategy including indication-specific product positioning, early warning market share shifts, clinical trial site selection, investigator recruiting, and accurate intelligence on market size and demand.

Other objects, features, and advantages of the present invention will become apparent from the drawings, detailed description of the invention, and the claims, below.

BRIEF DESCRIPTION OF THE DRAWINGS

FIGS. 1A, 1B, 1C, 1D and 1E are block and flow diagrams showing the overall structure and overall flow of the present invention in one embodiment.

DETAILED DESCRIPTION OF THE INVENTION

With reference to the drawings, in which like numerals represent like elements throughout, FIGS. 1A, 1B, 1C, 1D, 1E, 2A, 2B, and 2C illustrate a high-level combined block/flow diagram for the present invention. These figures represent both the elements of a block diagram for, as well as the steps performed by the system of, the present invention.

Referring to FIGS. 1A, 1B, 1C, 1D, 1E, 2A, 2B, and 2C, the primary processing that takes place in the present invention may be performed by, for example, a high-performance computing system, such as a Sun Microsystems ES10000 computer (at SITE 2). On a periodic basis, such as each day, seven days per week, a computing system at SITE 1 places healthcare claims data at step 103 via a secure connection 190 onto a computer system at SITE 1. This healthcare claims data may include, for example, pharmaceutical, 20 medical, and hospital claims 101 that have been "de-identified" at step 102 (explained in further detail below).

The claims data is de-identified at step 102 before it is sent to SITE 2, which includes applying a unique identifier, encrypting this identifier, and removing specific patient identifying fields. Data is then loaded into database tables (such as an Oracle database) at step 104 that also reside on SITE 2. At step 105, SITE 2 runs all processes for analyzing and consolidating the data and for transforming the resulting Oracle tables into OLAP cubes.

The cube building process may run on a different computer (such as SITE 2). Cubes are modeled using an OLAP product on a desktop computer under, for example, the Windows NT operating system.

The cube deployment process may run on a different computer (such as SITE 3). A computing system at SITE 2 places cubes and metadata files at step 106 via a secure connection to SITE 3. Processes run at step 107 at SITE 3 to place the cube on the production web site and to update the web site pages with the associated metadata.

Figure 3A:
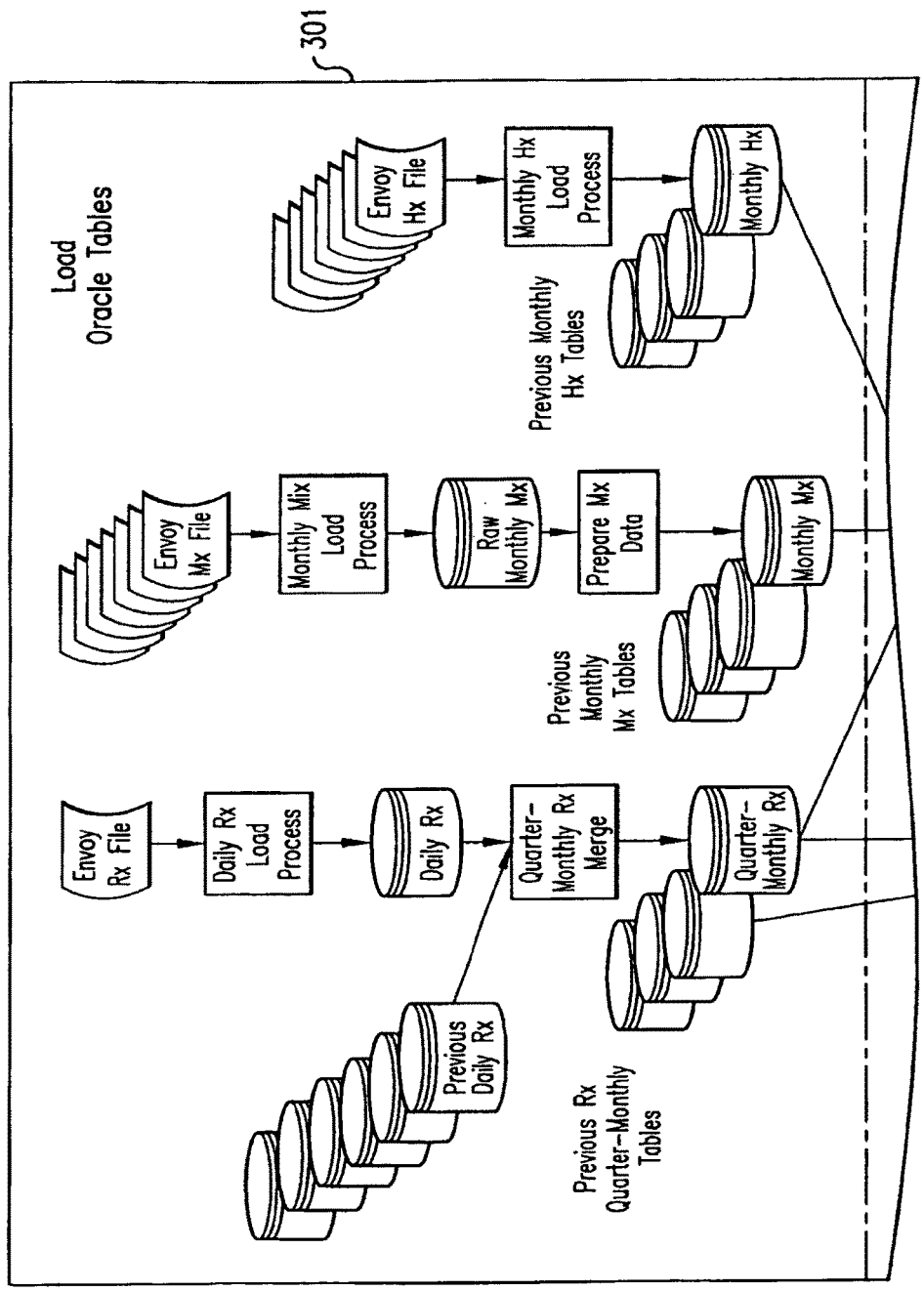
FIGS. 3A, 3B, and 3C illustrate a flow and relationship diagram, showing the overall flow and data relationship of the present invention.
Figure 3B:
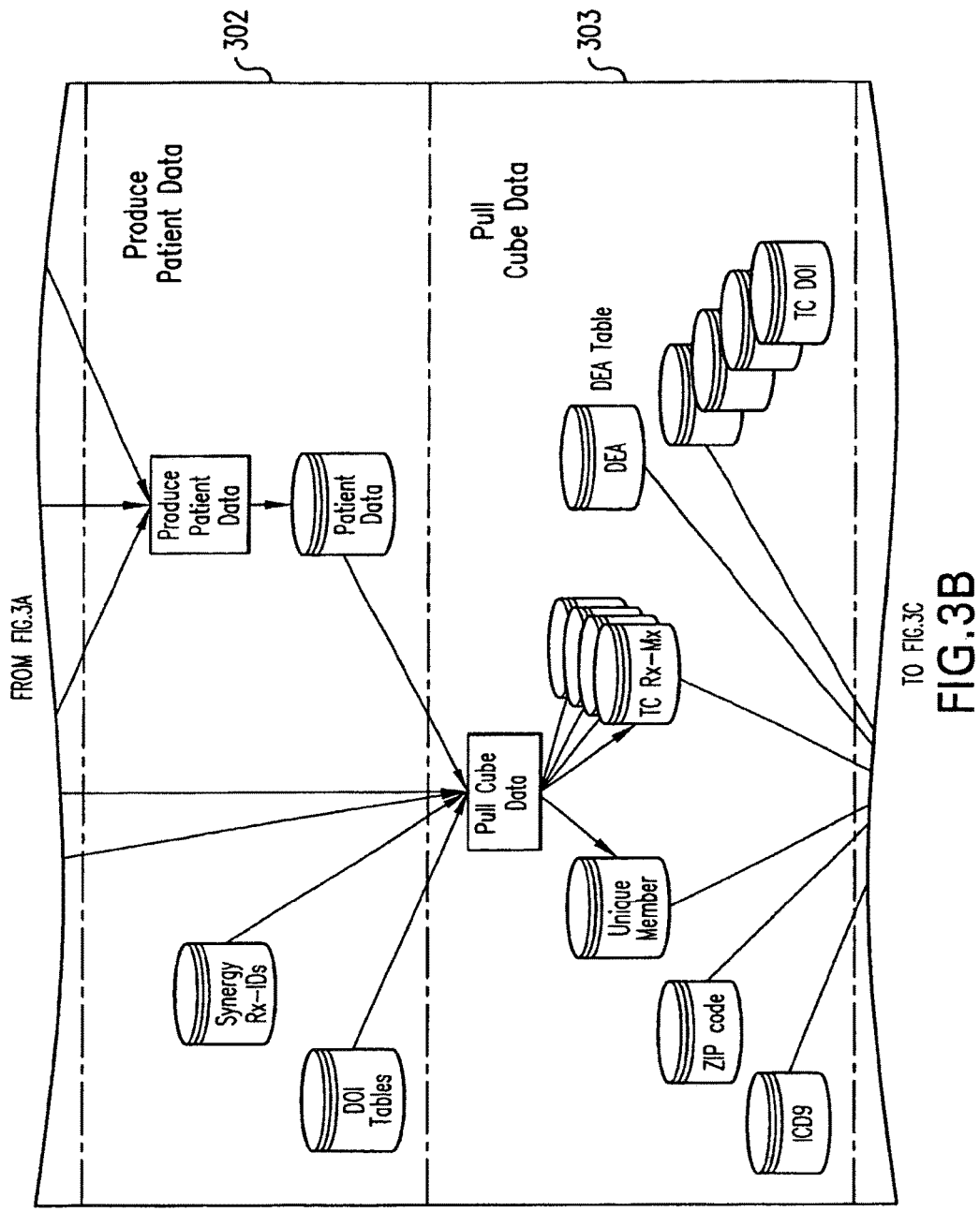
Figure 3C:
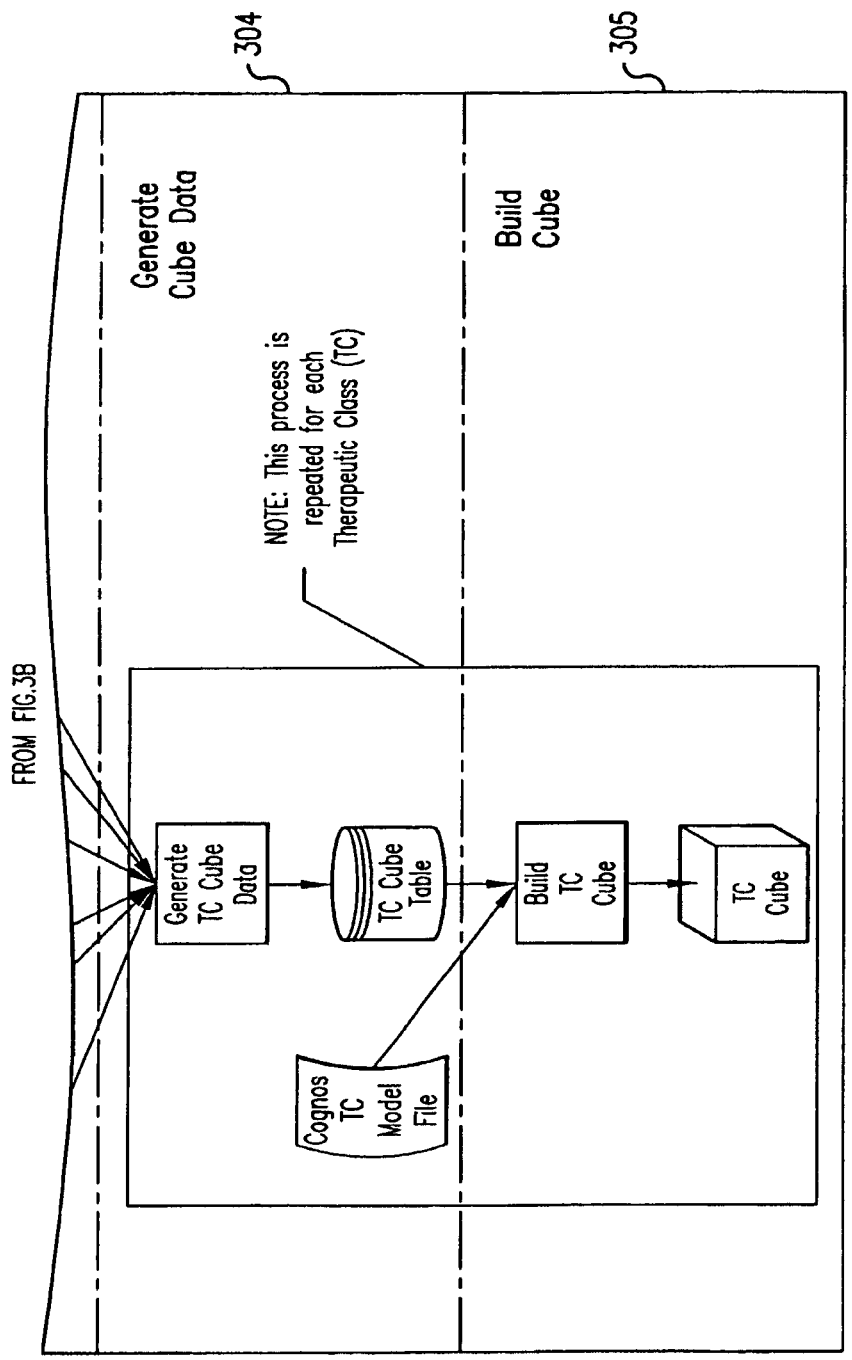

The present process performed at SITE 2 after obtaining data from the SITE 1 computer, making data ready for cube transformers, and then displaying it on the web 5 at SITE 3 can be logically divided into six major steps, as shown in FIGS. 3A, 3B, and 3C.

1. Load Oracle Tables (step 301)
2. Produce Patient Data (step 302)
3. Pull Cube Data (step 303)
4. Generate Cube Data (step 304)
5. Build Cube (step 305)
6. Automated Cube Deployment and Metadata Update Process All these processes are handled, maintained and executed at regular daily, weekly and monthly intervals. There are some processes which are done out of the routine process, such as generation of DOI, zip-state-region, ICD9, etc. tables. FIGS. 3A, 3B, and 3C show a high level overview of the processes used to create cubes.

1. Load Oracle Tables (Step 301)

The Load Oracle Tables process (step 301) can be divided into two logically different steps, daily and monthly processes, described in further detail below with respect to FIGS. 4-8. The daily routines convert the text format data supplied from SITE 1 into "RX" and "'Do Not Use Company Name (DNU)" daily Oracle tables. The monthly processes convert Hospital (HX) and Medical (MX) data into monthly Oracle tables. Note that all run times provided below correspond to approximate run times.

1.1 Daily Rx Load Process 401

Figure 4:
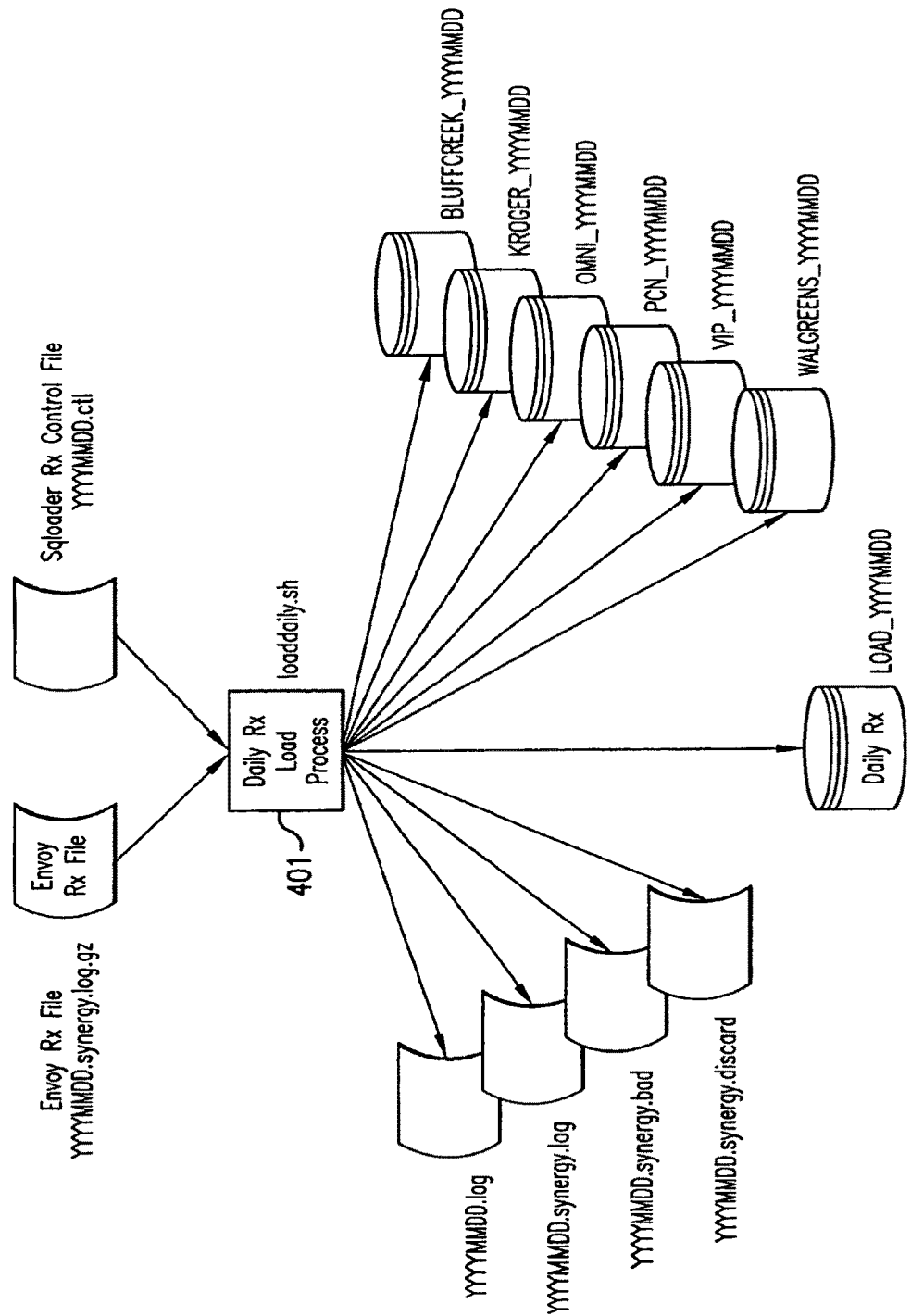
FIG. 4 illustrates the operation of the Daily Rx Load Process of the present invention.

The Daily Rx Load Process 401 is described below with respect to FIG. 4:

| | |
|---|---|
| Script Use | Loaddaily.sh is the unix shell script that uses the SQL Loader Rx Control File to Convert the Rx Text File from SITE 1 into LOAD_YYYYMMDD, {DNU}_YYYY MMDD Oracle tables after doing all the necessary number, char and date conversions. The {DNU} list contains BLUFFCREEK, KROGER, OMNI, PCN, VIP and WALGREENS. |
| Input | YYYYMMDD.synergy.log.gz, RX Control file, YYYYMMDD.ctl. |
| Output | LOAD_19991123, 24 etc. tables for each day of a month. WALGREENS_YYYYMMDD etc. tables for each DNU company. ../log/YYYYMMDD.log ../data.YYYYMMDD.synergy.log ../bad/YYYYMMDD.synergy.bad ../discard/YYYYMMDD.synergy.discard. |
| Frequency | Daily |
| Run Time | ~4 hours |

1.2 Monthly Mx Load Process 501

Figure 5:
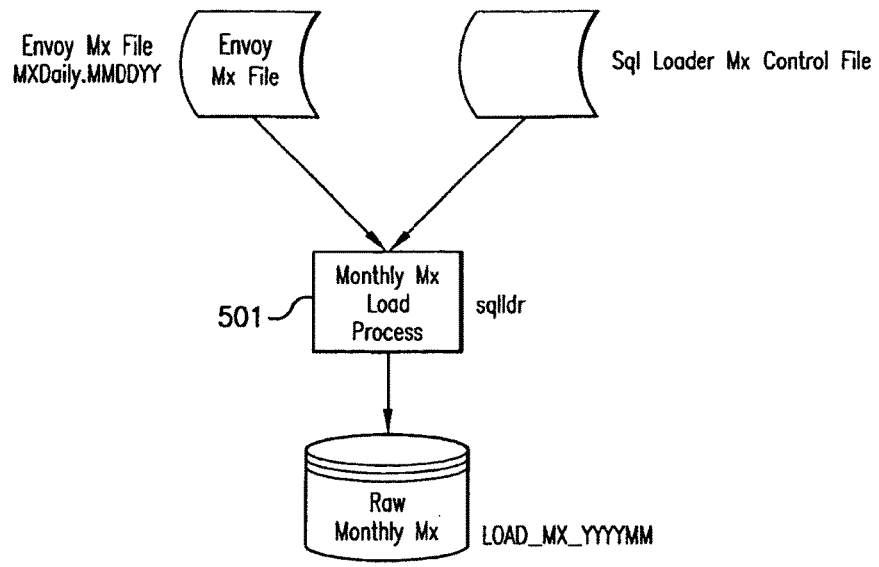
FIG. 5 illustrates the operation of the Monthly Mx Load Process of the present invention.

The Monthly Mx Load Process 501 is described below with respect to FIG. 5:

| | |
|---|---|
| Script Use | SQL LOADER process reads MXDaily.MMDDYY text file and control file to convert it into LOAD_MX_YYYYMM tables. |
| Input | /raid/4011/envoydata/mx/oct1999/data/MXDaily. 100199 MX Control file, yyyymmdd.ctl. |
| Output | LOAD_MX_YYYYMM table |
| Frequency | Monthly |
| Run Time | ~8 hours |

1.3 Load HX Text Data 601

Figure 6:
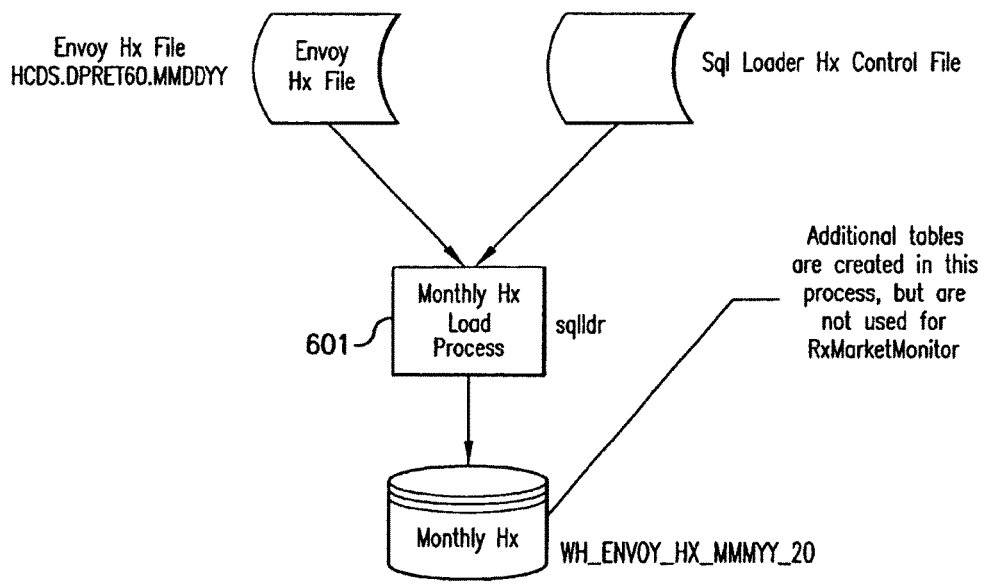
FIG. 6 illustrates the operation of the Monthly Hx Load Process of the present invention.

The Load HX Text Data Process 601 is described below with respect to FIG. 6:

| | |
|---|---|
| Script Use | SQL LOADER process reads MX text file and Control File to convert it into WH_ENVOY_HX_SEP99 tables. |
| Input | /raid/4011/envoydata/hx/sep1999/data/ MCDS.DPRET60.090199, HX Control file, yyyymmdd.ctl. |
| Output | WH_ENVOY_HX_SEP99_10..20..30..36..40..46..50.. 60..61..66..70..80..90 tables for HX. |
| Frequency | Monthly |
| Run Time | ~8 hours |

1.4 Quarter-Monthly Rx Merge 701

Figure 7:
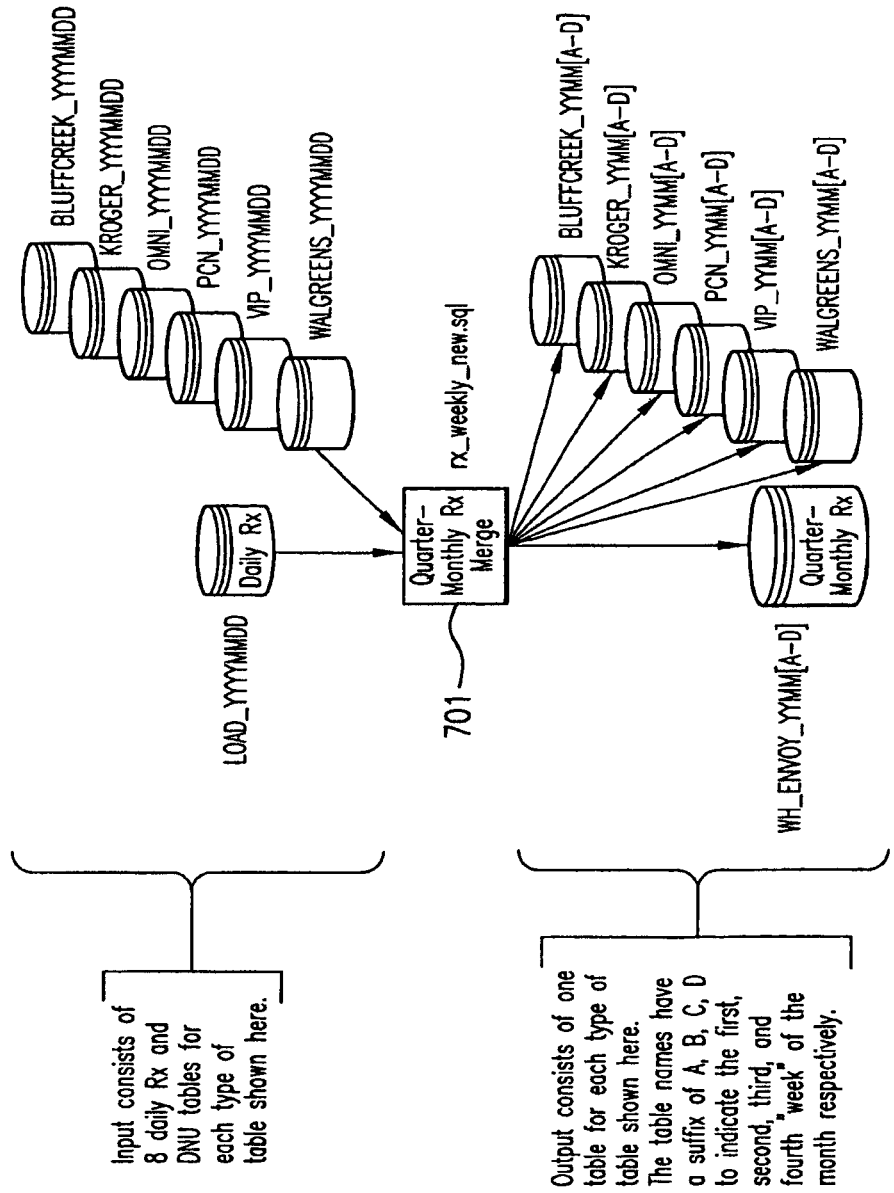
FIG. 7 illustrates the operation of Quarter Monthly Rx Merge Process of the present invention.

The Quarter-Monthly Rx Merge Process 701 is described below with respect to FIG. 7:

| | |
|---|---|
| Script Use | This process uses RX_Weekly_New.sql SQL script to combine all the daily (approx.. 8 days of tables) RX and DNU tables into quarter-monthly tables. |
| Input | LOAD_19991123..24 etc. tables for each day of a month WALGREENS_YYYYMMDD etc. tables for each "DNU" company |
| Output | WH_ENVOY_9911A..B..C..D etc. 4 tables for a month. WALGREENS_9911A..B..C..D like tables for each "DNU" company for a month. |
| Frequency | Monthly |
| Run Time | ~6 hours |

1.5 Prepare Mx Data (801)

Figure 8:
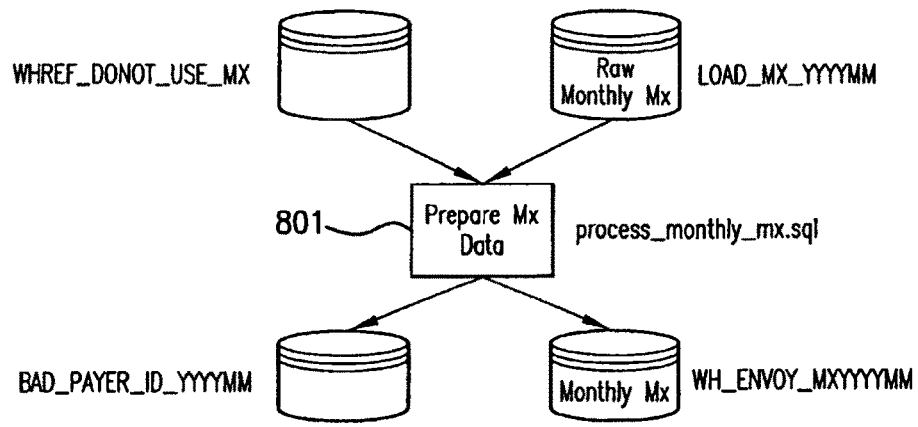
FIG. 8 illustrates the operation of the Prepare Mx Data Process of the present invention.

The Prepare mx Data Process 801 is described below with respect to FIG. 8:

| | |
|---|---|
| Script Use | This process uses Process_Monthly_MX.sql SQL script to validate and convert LOAD_MX_YYYYMM table data into required date, char and numbers. |
| Input | LOAD_MX_YYYYMM, WHREF_DONOT_USE_MX |
| Output | WH_ENVOY_YYYYMM BAD_PAYER_ID_YYYYMM |
| Frequency | Monthly |
| Run Time | |

2. Produce Patient Data (Step 302)

Figure 9:
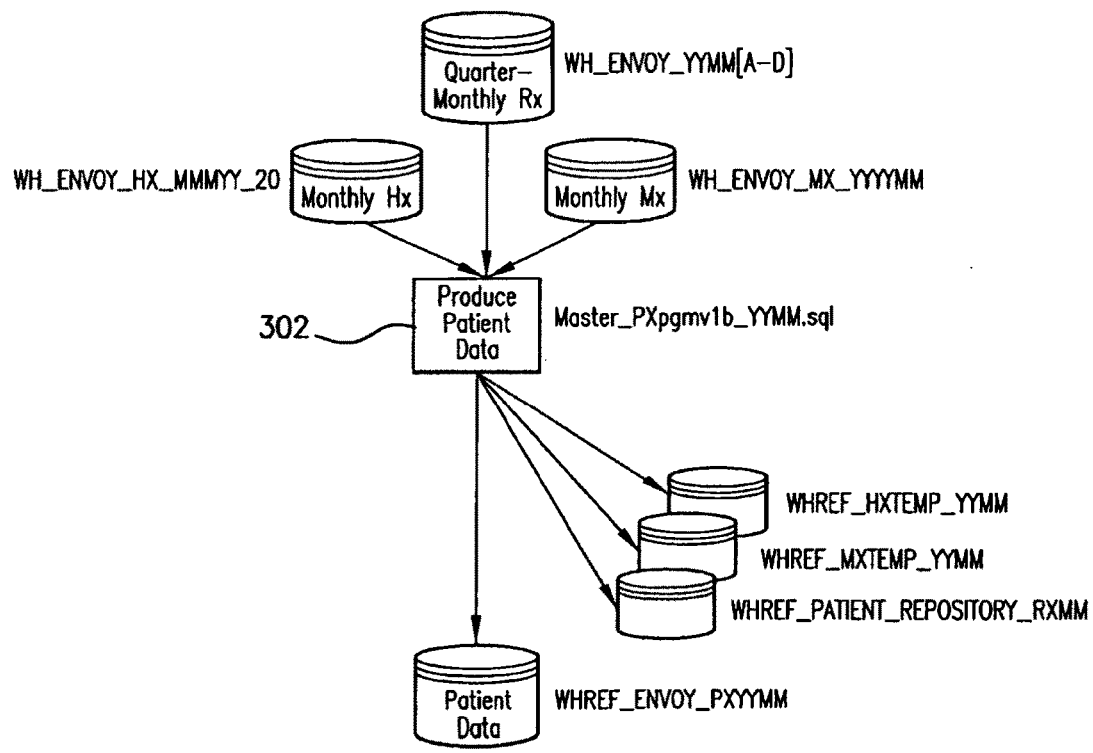
FIG. 9 illustrates the operation of the Produce Patient Data Process of the present invention.

The Produce Patient Data Process of step 302 (FIG. 3B) is described below in further detail with respect to FIG. 9:

| | |
|---|---|
| Script Use | This process uses Master_PXpgmv1b_9910.sql SQL script to combine weekly RX and monthly MX, HX tables to create a relational WHREF_ENVOY_PXYYMM table. |
| Input | WH_ENVOY_YYMMA..B etc., WH_ENVOY_MX_YYYYMM, WH_ENVOY_HX_MMMYY_20 tables. |
| Output | WHREF_PATIENT REPOSITORY RXMM, WHREF_MXTEMP_YYMM, WHREF_HXTEMP_YYMM, WHREF_ENVOY_PXYYMM tables. |
| Frequency | Monthly |
| Run Time | ~13 hours |

3. Pull Cube Data (Step 303)

Figure 10:
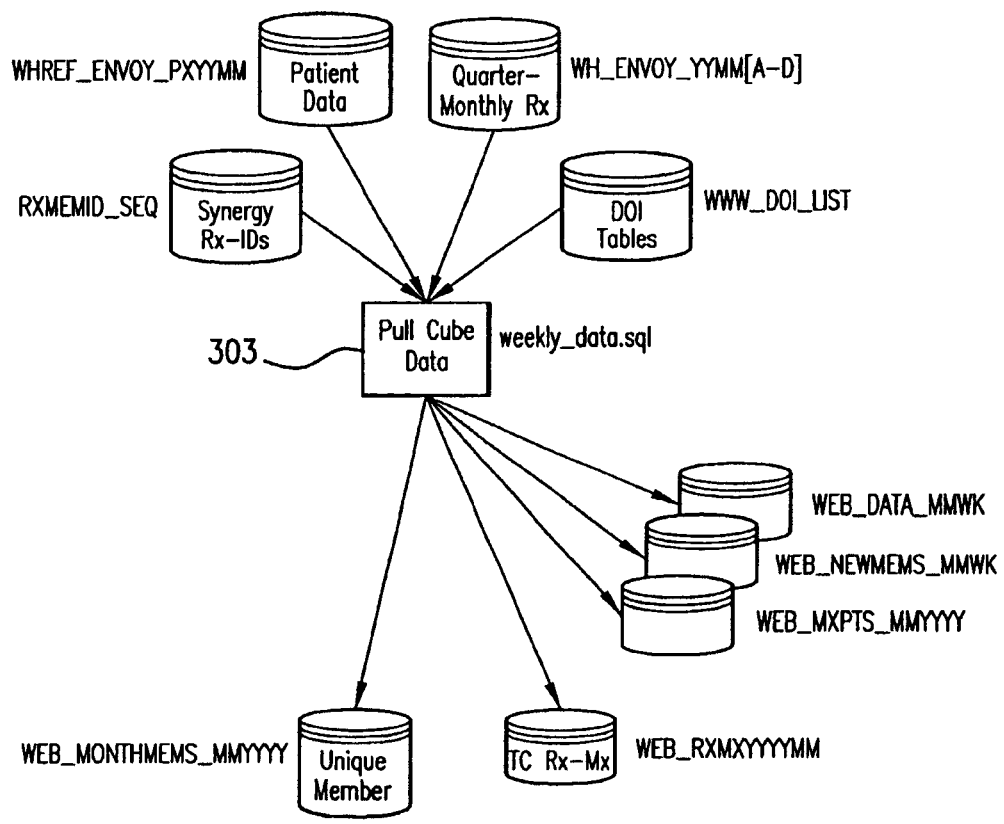
FIG. 10 illustrates the operation of the Pull Cube Data Process of the present invention.

The Produce Patient Data Process of step 303 (FIG. 3B) is described below in further detail with respect to FIG. 10:

This process uses a series of Oracle stored procedures to allow for error checking and audit logging. Logging for these procedures uses the MM_LOG table. These stored procedures are called from the Unix shell using shell script wrappers that input the necessary variable values. The stored procedures used are as follows:

mm00_init
mm01_set_vars
mm02_weekly_data_pull
mm03_memids
mm04_mx_diags 3.1 Audit Logging in Oracle Table MM_LOG
Structure of the MM_LOG Table.

| RUN_DATE | START_TIME | STOP_TIME | CUBE_NAME | PROCESS | RETURN_CODE | ERROR_CODE | DESCR |
|---|---|---|---|---|---|---|---|
| 10 Jul. 2000 | 8:26:37 | 8:26:38 | | mm00_init( ) | 0 | Completed | Procedure mm00_init( ) completed successfully |
| 10 Jul. 2000 | 8:26:38 | 8:26:38 | | mm01_set_vars( ) | 0 | Completed | Procedure mm01_set_vars( ) completed successfully |

-continued

| RUN_DATE | START_TIME | STOP_TIME | CUBE_NAME | PROCESS | RETURN_CODE | ERROR_CODE | DESCR |
|---|---|---|---|---|---|---|---|
| 11 Jul. 2000 | 8:26:38 | 12:35:49 | | mm02_weekly_data_pull( ) | 0 | | Completed Procedure mm02_weekly_data_pull( ) completed successfully. |
| 11 Jul. 2000 | 2:04:59 | 12:11:57 | | mm03_memids( ) | 0 | | Completed Procedure m03_memids( ) completed successfully |
| 11 Jul. 2000 | 1:07:32 | 11:23:46 | | mm04_mx_diags( ) | 1 | −904 | ORA-00904: invalid column name |

A record is added to MM_LOG for each process. The name of the process is in the PROCESS column. For cube specific processes, the name of the cube is in the CUBE_NAME column. When a process successfully completes, the RETURN_CODE column contains a 0; when there is an error, the RETURN_CODE column contains a 1.

3.2 Initialization

| | |
|---|---|
| Script Use | The mm00_init procedure initializes the environment for weekly Market Monitory cube processing. The mmOO.sh shell script calls the mm00_init procedure. |
| Input | None |
| Output | MM_LOG table truncated. MM_VARS table truncated. CUBE_DATA_TEXT table truncated. MM_LOG table - row inserted showing successful completion or error condition. |

3.3 Set Variables

| | | |
|---|---|---|
| Script Use | The mm01_set_vars procedure sets variables for the Rx Market Monitor weekly cube processing. The mm01.sh shell script calls the mm01_set_vars procedure with input variables set as text. The mm00_init procedure must already have been run. | |
| Input | p_run_date | Run date of pull as text 'YYYYMMDD'. |
| | p_start_date | Start date of pull as text 'YYYYMMDD'. |
| | p_end_date | End date of pull as text 'YYYYMMDD'. |
| | p_post_date | Post date of pull as text 'YYYYMMDD. |
| | p_acute_lookback | Acute lookback date as text 'YYYYMMDD'. |
| | p_chronic_lookback | Chronic lookback date as text 'YYYYMMDD". |
| Output | MM_VARS table - row inserted with this week's values as DATE datatype. MM_VARS_HIST table-row inserted with this week's values as DATE datatype. MM_LOG-row inserted showing successful completion or error condition. | |

3.4 Pull Weekly Data

| | | |
|---|---|---|
| Script Use | The mm02_weekly_data_pull procedure pulls one week of Rx data for weekly Rx Market Monitor cube processing. The mm02.sh shell script calls this procedure with the tablespace variable input set. The mm00_init and mm01_set_vars procedures must already have been run. | |
| Input | p_tablespace | Tablespace name as text. |
| | MM_VARS table | |
| | WH_ENVOY_YYMM where YYMM is the two character year and month from start_date in MM_VARS table. | |
| | WWW_MASTER_DOI | |
| Output | Last week's WEB_DATA_WEEK_PULL table is renamed to WEB_DATA_WEEK_PULL_YYYYMMDD where YYYYMMDD is one day before the start_date in MM_VARS table. New WEB-DATA-WEEK-PULL table is created in the WEB schema in the tablespace named in the p_tablespace parameter. The WEB_DATA_WEEK_PULL table contains Rx data from the start and end dates in the MM_VARS table. MM_LOG - a row is inserted to indicate either successful completion or error condition. | |

3.5 Get Memids

| | | |
|---|---|---|
| Script Use | The mm03_memids procedure accumulates six weeks of memids. The mm03.sh shell script calls this procedure and inputs the tablespace parameter. The mm00_init, mm01_set_vars, and mm02_weekly_data_pull procedures must already have been run. | |
| Input | p_tablespace | Tablespace name as text. |
| | MM_VARS table | |
| | ALL_MEM_TO CONVERT table | |
| | WEB_DATA_WEEK_PULL_V2 table | |
| | WEB_UMEMS_WEEK_V2_MONDD table where MONDD is the end_date from MM_VARS table as text. | |
| | WEB_UMEMS_WEEK_V2_MONDD[1-5] tables whereMONDD[1-5] are the previous five weeks of data. | |
| | RXMEMID SEQ table | |
| Output | WEB_UMEMS_WEEK_V2_MONDD table is created where MONDD is start_date in MM_VARS table minus one day. WEB_UMEMS_WEEK_PULL is created with data for current week and previous 5 weeks. | |
| | MM_LOG - a row is inserted to indicate either successful completion or error condition. | |

3.6 Get Mx Diagnoses

| | | |
|---|---|---|
| Script Use | The mm04_mx_diags procedure gets diagnoses information from Mx tables for weekly processing. The mm04.sh shell script executes this procedure with the tablespace input variable set. The mm00_init, mm01_set_vars, mm02_weekly_data_pull, and mm03_memids procedures must already have been run. | |
| Input | p_tablespace | Tablespace name as text. |
| | MM_VARS table | |
| | WEB_UMEMS_WEEK_PULL_V2 table | |
| | MASTER PX table | |
| | WEB_MXPTS_WEEK_PULL_V2 table | |
| | WH_ENVOY_MX_YYYYMM[1-3] tables where YYYYMM[1-3] are the current month and two prior months of data. | |

| | WEB_RXMX_WEEK_PULL_V2 table |
| --- | --- |
| | RXMEMID_SEQ table |
| Output | ACUTE_RXMX table - records from the week are appended. |
| | CHRONIC_RXMX table- records from the week are appended. |
| | MM_LOG table - row inserted to indicate either successful completion or error condition. |

4. Generate TC Cube Data (Step 304)

Figure 11:
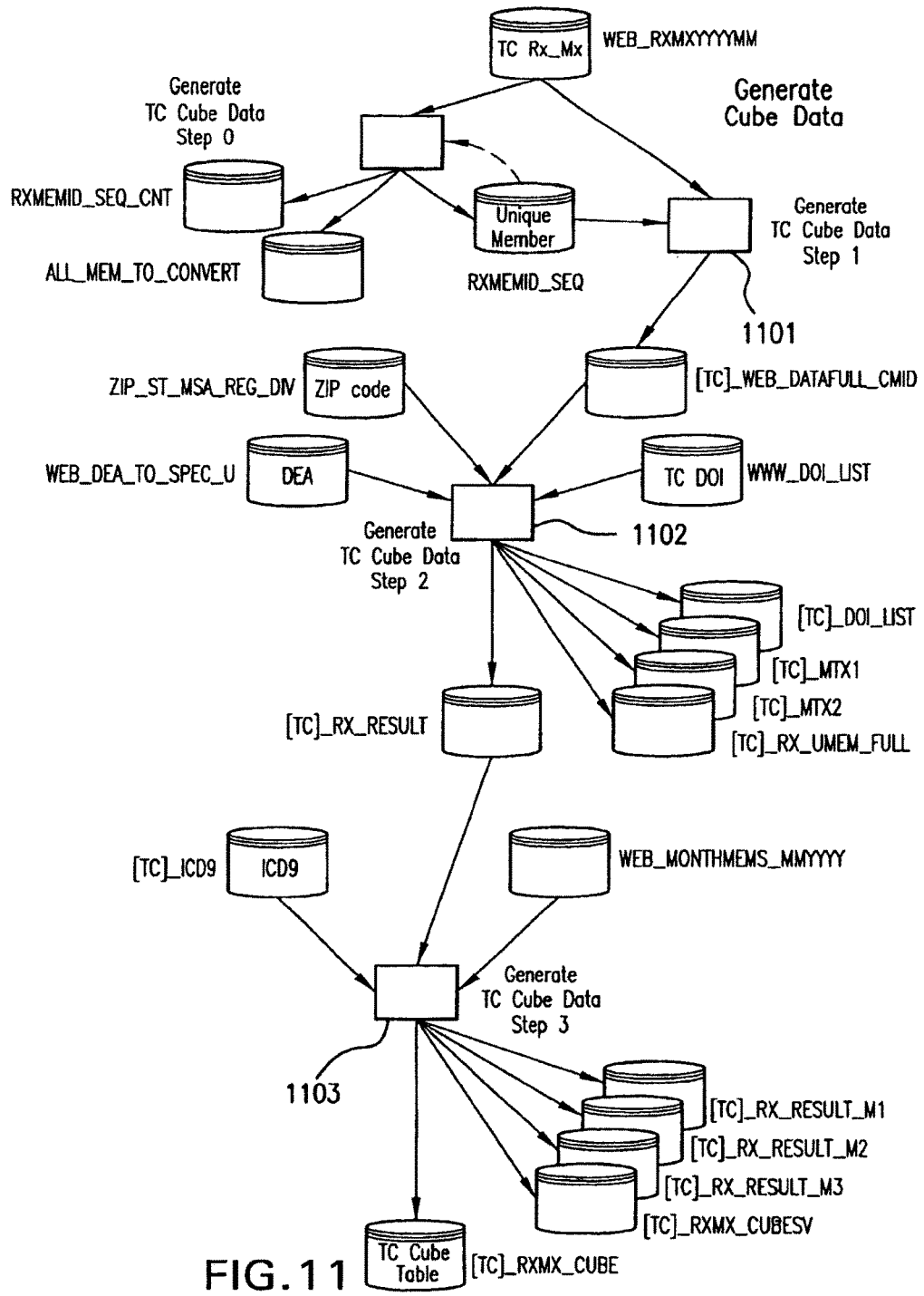
FIG. 11 illustrates the operation of the Generate TC Cube Data Process of the present invention.

The Generate TC Cube Data Process of step 304 (FIG. 3C) is described below in further detail with respect to FIG. 11:

The Generate TC Cube Data Process 304 uses three Oracle stored procedures to generate a cube table which will be further used by data transformers to build a COGNOS readable multi-dimensional formatted cube structure. The last stored procedure updates statistics for each cube. The stored procedures are as follows:

mm05_step1 mm06_step2 mm07_step3 mm08_cube_metadata

4.1 Process Step 1101 (Step 1)

| Script Use | The mm05_step1 procedure must be run for each therapeutic class. This procedure inserts records into the CMID_V2_CLASS table where CLASS is the p_class specified. The mm00_init, mm01_set_vars, mm02_weekly_data_pull, mm03_memids, and mm04_mx_diags procedures must already have been run. |
| --- | --- |
| Input | p_class            Class name. |
| | p_tablespace     Tablespace name as text. |
| | p_lookback       Number of days of lookback |
| | p_condition        "ACUTE" or "CHRONIC" |
| | MM_VARS table |
| | WEB_DATA_WEEK_PULL_V2 table |
| | CUBE_V2_LIST table |
| | CMID_V2_CLASS table where CLASS is the p_class. |
| Output | Records inserted into CMID_V2_CLASS table where CLASS is the p_class. |
| | New CMID_V2_CLASS_TMP table is created where CLASS is the p_class. |
| | MM_LOG table- row inserted to indicate either successful completion or error condition. |

4.2 Process Step 1102 (Step 2)

| Script Use | The mm06_step2 procedure must be run for each therapeutic class. This procedure inserts records into the RX_RESULT_V2_CLASS table where CLASS is the p_class specified when the procedure is called. The mm00_init, mm01_set_vars, mm02_weekly_data_pull, mm03_memids, mm04_mx_diags, and mm05_step1 procedures must already have been run. |
| --- | --- |
| Input | p_class            Class name. |
| | p_tablespace     Tablespace name as text. |
| | p_lookback       Number of days of look back |
| | p_condition        "ACUTE" or "CHRONIC" |
| | MM_VARS table |
| | CMID_V2_CLASS_TMP table where CLASS is the p_class. |
| | CMID_V2_CLASS table where CLASS is the p_class. |
| | RX_RESULT_TEMP_CLASS table where CLASS is the p_class. |
| | ZIP_ST_MSA_REG_DIV table |
| | WEB_DEA_TO_SPEC_U |
| Output | New records are inserted into RX_RESULT_V2_CLASS where CLASS is p_class. |
| | MM_LOG table - row inserted to indicate either successful completion or error condition. |

4.3 Process Step 1103 (Step 3)

| Script Use | The mm07 step3 procedure must be run for each therapeutic class. This procedure creates a new RXMX_CUBE_V2_CLASS table where class is the p_class specified. The mm00_init, mm01_set_vars, mm02_weekly_data_pull, mm03_memids, mm04_mx_diags, mm05_step1, and mm06_step2 procedures must already have been run. |
| --- | --- |
| Input | p_class            Class name. |
| | p_tablespace     Tablespace name as text. |
| | p_lookback       Number of days of lookback |
| | p condition        "ACUTE" or "CHRONIC" |
| | RXMX_CONDITION_V2 table where CONDITION is the p_condition. |
| | RX_RESULT_V2_CLASS table where CLASS is the p_class. |
| | ICD9 V2_CLASS table where CLASS is the p_class. |
| | RX_RESULT_V2_CLASS_M table where CLASS is the p_class. |
| Output | New RXMX_CUBE_V2_CLASS table is created where CLASS is p_class. |
| | MM_LOG table - row inserted to indicate either successful completion or error condition. |

4.4 Generate Cube Metadata

| Script Use | The mm08 cube_metadata procedure must be run for each therapeutic class. This procedure updates the CUBE_DATA table for each cube. The mm00_init, mm01_set_vars, mm02_weekly_data_pull, mm03_memids, mm04_mx_diags, mm05_step1, mm06_step2 and mm07 step3 procedures must already have been run. |
| --- | --- |
| Input | p_class            Class name. |
| | MM_VARS table |
| | CUBE_DATA table where CLASS is the p_class. |
| Output | CUBE_DATA_TEXT table is appended where CLASS is p_class. |
| | MM_LOG table - row inserted to indicate either successful completion or error condition |

5. Build Cube (Step 305)

Figure 9A:
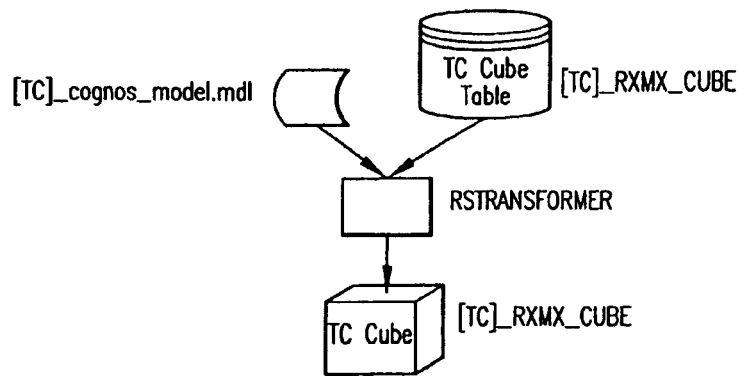
FIG. 9A illustrates the operation of the RSTRANSFORMER process of the present invention.

The Build Cube Process of step 305 (FIG. 3C) is described below in further detail with respect to FIG. 9A:

This process uses a C program to create a cube for each therapeutic class. Each cube is FTP'd to the server of SITE 3. Metadata for each cube is spooled to a text file and FTP'd to the SITE 3 server. The same text files may be concatenated and sent via email to the web developer of SITE 2.

5.1 Build Cube

| Script Use | The program RSSERVER is repeated for each of the therapeutic classes and called by the script mmv2_ 'class name' .sh. |
| --- | --- |
| | Data Transformers uses Model Structure and OBES_RX_CUBE |
| | Oracle table (built in above process) to finally build a CUBE for each of the therapeutic class. This Cube is then used by COGNOS to show requested information on the Web. |
| Input | OBES_RXMX_CUBE |
| Output | Cube for a OBES Class |
| Frequency | On Request |
| Run Time | ~8 hours |

5.2 FTP Cube to SITE 3 Server

| | |
|---|---|
| Script Use | The transfer_mm_cube.sh script renames a cube and puts a copy into directory /raid4011/cubes/transfer where it will automatically be FTP'd to the SITE 3 server. This script is run in parallel for each class (class corresponds to cube). |

5.3 Approve Cube

| | |
|---|---|
| Script Use | The approve_cube script is run manually for each cube after quality assurance has been performed. This script is run in parallel for each class (class responds to cube). |

5.4 Create Metadata Text File/FTP to SITE 3 Server

| | |
|---|---|
| Script Use | The process gen_mm_file.sql is called by gen_mm_file.sh to spool metadata for a cube to a text file. The text file is put into a directory where it is automatically FTP'd to the SITE 3 server. This script is run in parallel for each class. All procedures to pull cube data must have been successfully completed and the metadata must exist in the Oracle tables cube_data and cube_data_text. |

5.5 E-Mail Metadata to Web Developer

| | |
|---|---|
| Script Use | The email_meta.sh script will e-mail metadata to a SITE 2 Web Developer. This script is run in parallel for each class (class corresponds to cube). |

6. Automated Cube Deployment and MetaData Update Process

Automated processes exist on the OnLine Analytical Processing (OLAP) host machine to deploy data cubes (such as QUINTERNET™ Series, from Quintiles Transnational Corp.) to the production web site, cubes ready for Quality Assurance (QA) verification, as well as to automatically update "metadata" on production web pages. This enables production cube deployments and web page updates to occur during off-peak hours without any manual intervention.

As a QUINTERNET™ Series data cube is created, the cube is sent via a secure connection to the host machine. The cube is then automatically "served up" to the QA location on the web, to which only authorized personnel have access.

For each cube approval, a "metadata" file is transmitted from the SITE 2 server, via a secure connection, to the host machine in a specific location (directory within a file system). This secure transmission may occur after a data cube has passed the QA verification.

The metadata file contains statistical information about the specific cube (e.g.—date that cube contains data through, number of records, number of patients, etc.). Several times each night, an automated process may be initiated which checks for the presence of a metadata file and a corresponding data cube file. If matching files for a specific cube exist, the process automatically "serves" up this cube into production for access via the web pages. In addition, the HTML page which contains the metadata for the cube is updated with the metadata contained in the metadata file.

The server at, for example, SITE 3 may prepare and maintain HTML template files for each QUINTERNET™ Series cube. These files contain the base HTML used to create each cube's web page. Instead of the actual metadata values that will populate the cubes' web pages, the HTML template files may contain placeholder tags. These placeholder tags are replaced by data values supplied by SITE 2 in metadata files.

SITE 2 transfers the template files and the metadata files to a host via FTP. The metadata files are transferred to the host each time a cube is approved. Template files are maintained for each QUINTERNET™ Series cube and are updated by SITE 2 as necessary so that a current version of each cube's template file is always available for processing on the host.

After a cube has been updated, reviewed for quality and approved by the operator of SITE 2, SITE 2 transfers a metadata file for that cube to the host via FTP. The metadata files contains the same tags found in the HTML template file for each cube. Each of these tags is coupled with a value that will be substituted for the placeholder tag in the HTML template file.

An event-driven file processing script runs periodically via cron, a unix scheduling system, on the host. If the file processing script detects the existence of a designated flag file, a script called enable_cube.ksh is run. The enable_cube.ksh script calls a Perl script, replaceHtmlMetaTags.pl, passing it the name of the cube being processed and the name of the related metadata file. The enable_cube.ksh script also updates the metadata file with a tag/value pair representing the date the updated cube is being deployed.

Figure 1A:
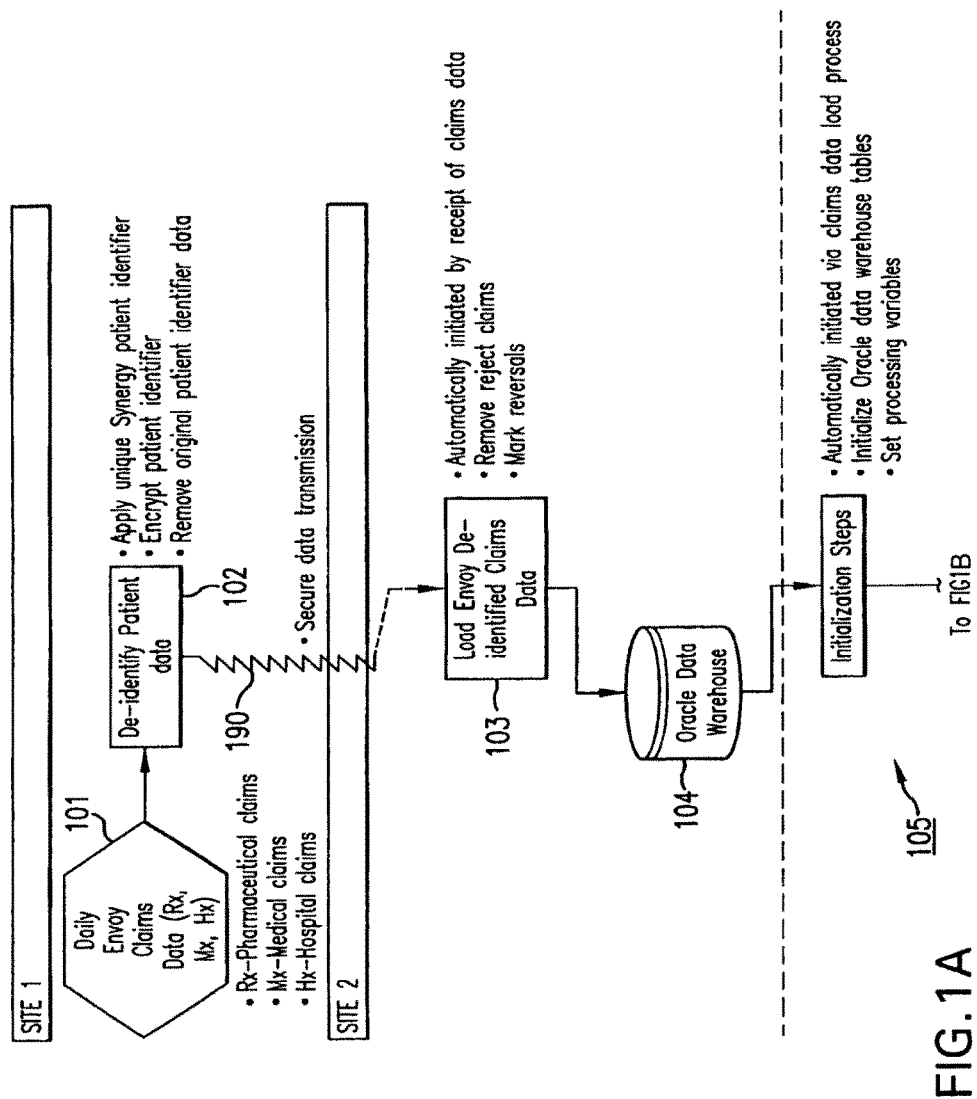
Figure 1B:
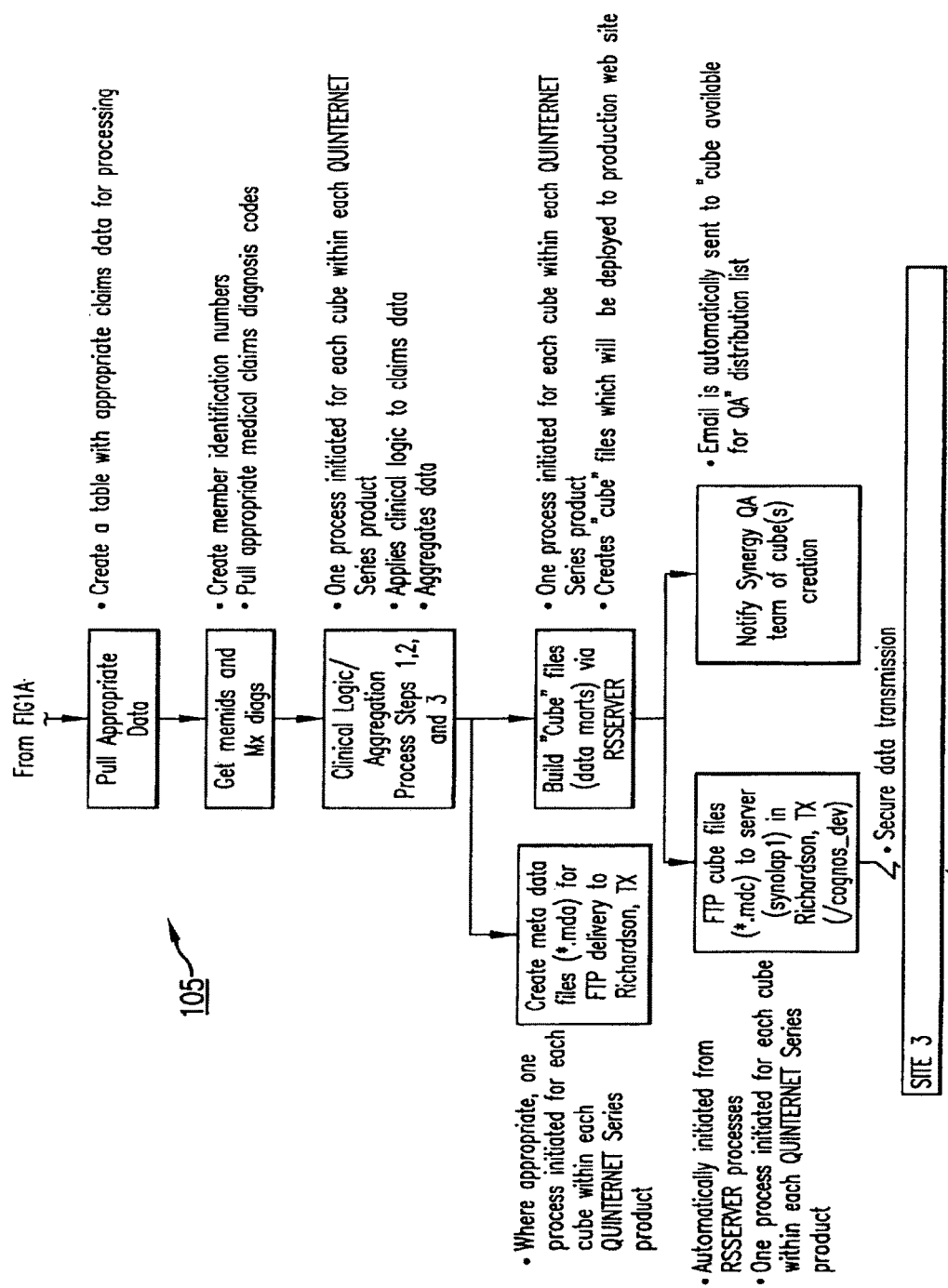
Figure 1D:
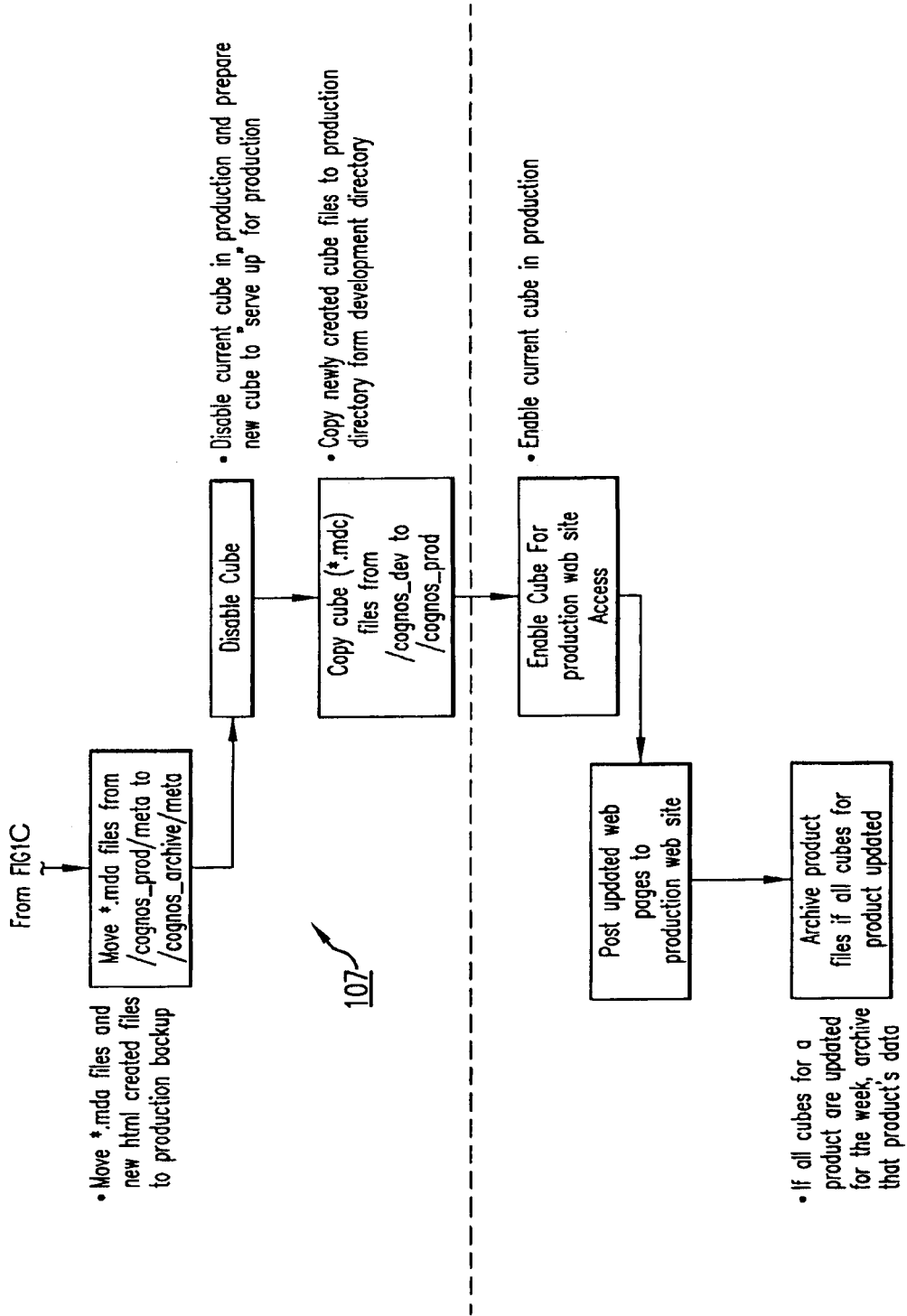
Figure 1E:
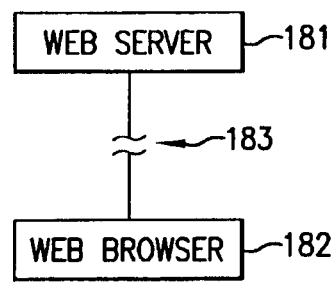
Figure 2A:
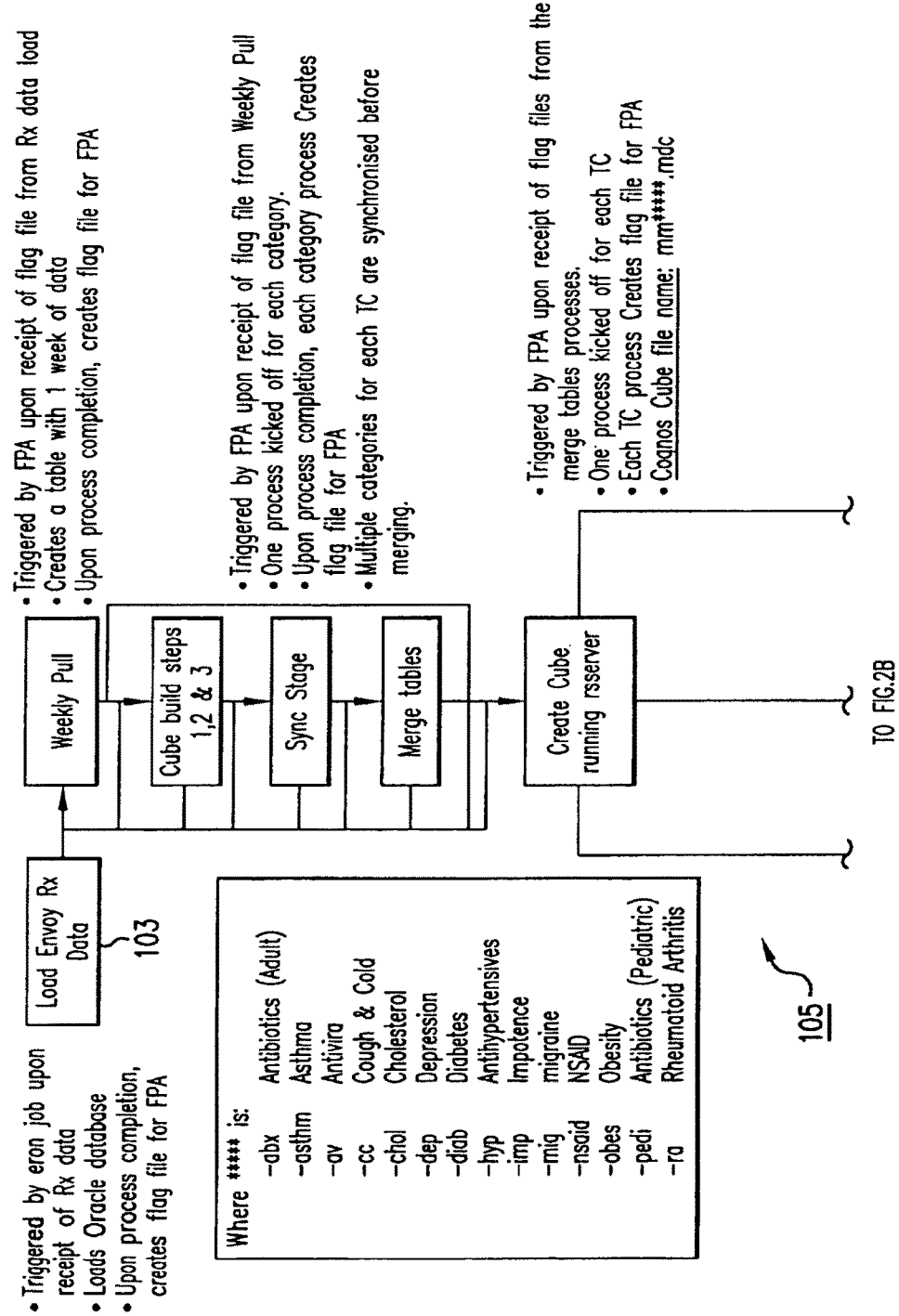
FIGS. 2A, 2B, and 2C are block and flow diagrams showing the overall structure and overall flow of the present invention in one embodiment.
Figure 2B:
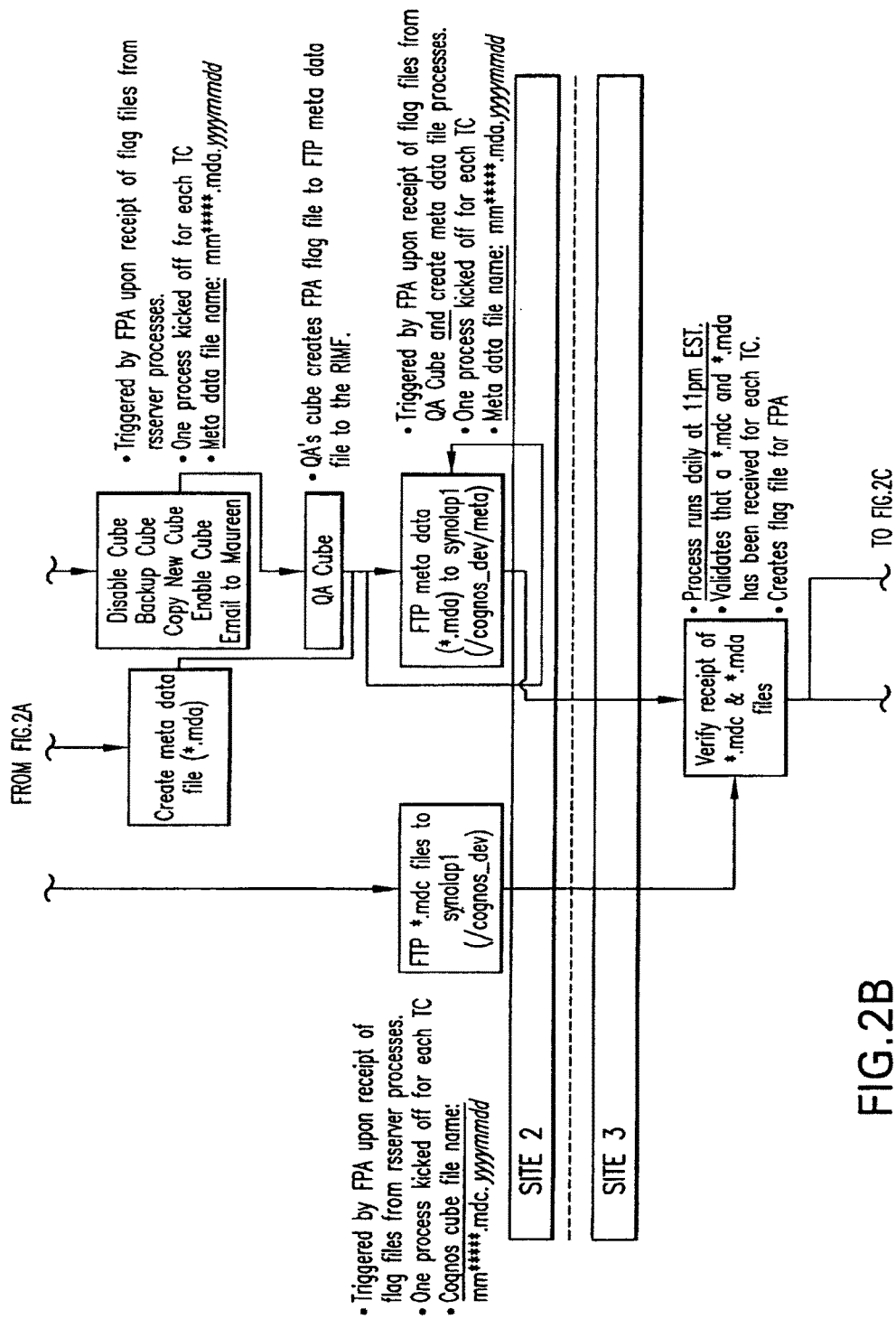
Figure 2C:
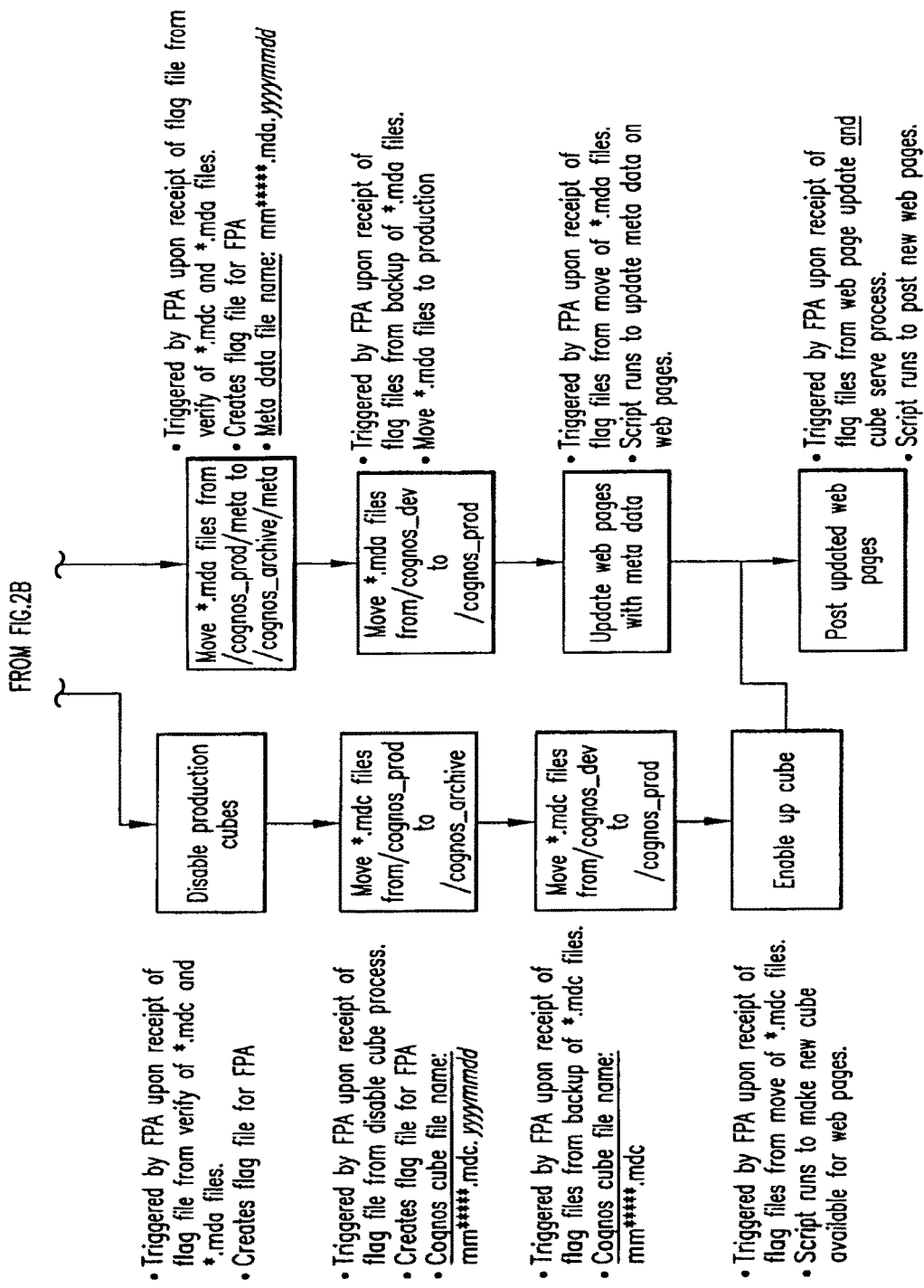

The purpose of the replaceHtmlMetaTags.pl script is to automatically generate HTML pages for the QUINTERNET™ Series products. The replaceHtmlMetaTags.pl script substitutes the values in the metadata file for the placeholder tags in the template and saves the resulting output in an HTML file. Referring to FIG. 1E, the enable_cube.ksh script then promotes the updated HTML file(s) to SITE 3's web server 181 thus making it available via, for example, the Internet 183, to users of web browsers 182 operating on client computers.

The present invention may be implemented with a processing schedule defined in many ways. For example, the schedule may be on a weekly or monthly basis, depending upon the needs of the implementation. At times, special requests may be required and the ability to process data and create cubes on an ad hoc basis exists.

While there has been shown the preferred embodiment of the present invention, it is to be understood that certain changes can be made in the forms and arrangements of the elements of the system and the steps of the method without departing from the spirit and scope of the invention as is set forth in the Claims.

A system for analyzing de-personalized health care data includes health care databases and a processor connected to the health care databases. The health care data bases each include at least one record, and each record includes a depersonalized yet unique patient identifier associated with a patient. The de-personalized patient identifier is common for a specific patient across several health care databases. According to one embodiment, the de-personalized health care data can be pharmaceutical claims data.

The processor performs the steps of: (i) receiving records from the health care databases; (ii) querying the records received from the health care databases, based upon selected person-level criteria; and (iii) generating at least one report based upon the results of the querying step. In another embodiment, the generating step performed by the processor can include the step of manipulating the results for display in specific views that satisfy specific analytical goals. In yet another embodiment, the generating step performed by the processor can include the step of displaying the report in a tabular format.

A method for analyzing de-personalized health care data within health care databases, wherein the health care databases each include at least one record. Each record includes a depersonalized yet unique patient identifier associated with a patient. The de-personalized patient identifier is common for a specific patient across the health care databases. According to one embodiment, the de-personalized health care data includes pharmaceutical claims data. The method includes the steps of: (a) receiving records from the health care databases; (b) querying the records received from the health care databases; and (c) generating at least one record based upon the results of the querying step. In one embodiment, the generating step includes the step of manipulating the results for display in specific views that satisfy specific analytical goals. In another embodiment, the generating step includes the step of displaying the report in a tabular format.

What is claimed is:

1. A system for analyzing de-personalized health care data, comprising:
   (a) a plurality of health care databases, the plurality of health care databases each including at least one record, each record including a de-personalized yet unique patient identifier associated with a patient, whereby the de-personalized patient identifier is a common value identifying a specific patient across a plurality of health care databases that are associated with distinct database systems of different organizations;
   (b) one or more processors in communication with a first of the health care databases, and one or more storage devices storing instructions that, when executed by the one or more processors, cause the one or more processors to perform operations comprising:
      (i) receiving a new record from at least one of the plurality of healthcare databases, the new record comprising a plurality of identification fields uniquely identifying a patient associated with the new record;
      (ii) concatenating, into a combined textual representation, text from each of the accessed plurality of identification fields included in the new record,
      (iii) generating at least one de-personalized yet unique patient identifier associated with the patient by encrypting the concatenated text of the combined textual representation; and
      (iv) storing, in a first of the health care databases, at least a portion of the received new record in association with the least one de-personalized yet unique patient identifier.

2. A method for de-identifying health care data comprising:
   receiving a new record from at least one of a plurality of health care databases, the new record comprising a plurality of identification fields uniquely identifying a patient associated with the new record;
   concatenating, into a combined textual representation, text from each of the plurality of identification fields included in the new record,
   generating at least one de-personalized yet unique patient identifier associated with the patient by encrypting the concatenated text of the combined textual representation, the at least one de-personalized yet unique patient identifier representing a common value identifying the patient across a plurality of health care databases that are associated with distinct database systems of different organizations; and
   storing, in a first of the health care databases, at least a portion of the received new record in association with the least one de-personalized yet unique patient identifier.

3. A non-transitory computer-readable medium encoded with instructions that, when executed by one or more processors, cause the one or more processors to perform operations comprising:
   receiving a new record from at least one of a plurality of health care databases, the new record comprising a plurality of identification fields uniquely identifying a patient associated with the new record;
   concatenating, into a combined textual representation, text from each of the plurality of identification fields included in the new record,
   generating at least one de-personalized yet unique patient identifier associated with the patient by encrypting the concatenated text of the combined textual representation, the at least one de-personalized yet unique patient identifier representing a common value identifying the patient across a plurality of health care databases that are associated with distinct database systems of different organizations; and
   storing, in a first of the health care databases, at least a portion of the received new record in association with the least one de-personalized yet unique patient identifier.

4. The system of claim 1, wherein the plurality of identification fields included in the new record comprise one or more of a patient's name, address, social security, contact number, date of birth, or gender.

5. The system of claim 1, wherein the one or more processors execute instructions that cause the one or more processors to perform operations comprising:
   identifying one or more records stored in the first of the health care databases that include the at least one de-personalized yet unique patient identifiers; and
   generating a report based on data included in the identified one or more records.

6. The system of claim 1, wherein the new record comprises one or more healthcare fields that include at least one of pharmaceutical claims data, medical claims data, or hospital claims data.

7. The system of claim 1, wherein the operations further comprise:
   removing, from the portion of the new record that is stored in associated with the at least one de-personalized yet unique patient identifier, information other than the at least one de-personalized yet unique patient identifier that identifies the patient.

8. The system of claim 1, wherein:
   the plurality of identification fields comprises a patient last name field and a patient birthdate field; and
   concatenating the text from each of the plurality of identification fields included in the new record comprises concatenating, into the combined textual representation, a first text segment corresponding to a value stored in the patient name field and a second text segment corresponding to a value stored in the patient birthdate field.

9. The method of claim 2, wherein the plurality of identification fields included in the new record comprise one or more of a patient's name, address, social security, contact number, date of birth, or gender.

10. The method of claim 2, comprising:
   identifying one or more records stored in the first of the health care databases that include the at least one de-personalized yet unique patient identifiers; and
   generating a report based on data included in the identified one or more records.

11. The method of claim 2, wherein the new record comprises one or more healthcare fields that include at least one of pharmaceutical claims data, medical claims data, or hospital claims data.

12. The computer-readable medium of claim 3, wherein the plurality of identification fields included in the new record comprise one or more of a patient's name, address, social security, contact number, date of birth, or gender.

13. The computer-readable medium of claim 3, wherein the operations comprise:
   identifying one or more records stored in the first of the health care databases that include the at least one de-personalized yet unique patient identifiers; and
   generating a report based on data included in the identified one or more records.

14. The computer-readable medium of claim 3, wherein the new record comprises one or more healthcare fields that include at least one of pharmaceutical claims data, medical claims data, or hospital claims data.

* * * * *